US010758518B2

(12) United States Patent
Booher

(10) Patent No.: US 10,758,518 B2
(45) Date of Patent: Sep. 1, 2020

(54) COMPOUNDS AND COMPOSITIONS FOR TREATING HEMATOLOGICAL DISORDERS

(71) Applicant: Curis, Inc., Lexington, MA (US)

(72) Inventor: Robert Booher, Davis, CA (US)

(73) Assignee: Curis, Inc., Lexington, MA (US)

(*) Notice: Subject to any disclaimer, the term of this patent is extended or adjusted under 35 U.S.C. 154(b) by 0 days.

(21) Appl. No.: 16/176,940

(22) Filed: Oct. 31, 2018

(65) Prior Publication Data
US 2019/0134010 A1 May 9, 2019

Related U.S. Application Data

(60) Provisional application No. 62/579,502, filed on Oct. 31, 2017.

(51) Int. Cl.
A61K 31/437 (2006.01)
A61K 31/5377 (2006.01)
A61K 31/4545 (2006.01)
A61K 45/06 (2006.01)
A61P 35/02 (2006.01)
A61K 31/496 (2006.01)

(52) U.S. Cl.
CPC ........ A61K 31/437 (2013.01); A61K 31/4545 (2013.01); A61K 31/496 (2013.01); A61K 31/5377 (2013.01); A61K 45/06 (2013.01); A61P 35/02 (2018.01)

(58) Field of Classification Search
None
See application file for complete search history.

(56) References Cited

U.S. PATENT DOCUMENTS

| 5,494,911 | A | 2/1996 | Bartlett et al. |
|---|---|---|---|
| 7,338,950 | B2 | 3/2008 | Kelly et al. |
| 9,732,095 | B2 | 8/2017 | Gummadi et al. |
| 9,855,273 | B2 | 1/2018 | Starczynowski et al. |
| 10,047,104 | B2 | 8/2018 | Gummadi et al. |
| 10,160,753 | B2 | 12/2018 | Gummadi |
| 2005/0192293 | A1 | 9/2005 | Kelly et al. |
| 2006/0014747 | A1 | 1/2006 | Krueger et al. |
| 2006/0160861 | A1 | 7/2006 | Bohlmann et al. |
| 2009/0069288 | A1 | 3/2009 | Breinlinger et al. |
| 2010/0160388 | A1 | 6/2010 | Brotherton-Pleiss et al. |
| 2010/0210619 | A1 | 8/2010 | Bombrun et al. |
| 2011/0224137 | A1 | 9/2011 | Ting et al. |
| 2012/0015962 | A1 | 1/2012 | Arora et al. |
| 2012/0053345 | A1 | 3/2012 | Ericson et al. |
| 2016/0326151 | A1 | 11/2016 | Gummadi et al. |
| 2017/0152263 | A1 | 6/2017 | Gummadi et al. |
| 2018/0022758 | A1 | 1/2018 | Gummadi et al. |
| 2018/0201609 | A1 | 7/2018 | Gummadi et al. |
| 2018/0208605 | A1 | 7/2018 | Gummadi et al. |

FOREIGN PATENT DOCUMENTS

| CN | 103608017 A | 2/2014 |
|---|---|---|
| EP | 1627869 A1 | 2/2006 |
| GB | 2406856 A | 4/2005 |
| JP | 2008-239617 A | 10/2008 |
| KR | 20130128693 A | 11/2013 |
| WO | WO-2004/007457 A2 | 1/2004 |
| WO | WO-2004/007458 A1 | 1/2004 |
| WO | WO-2004/098518 A2 | 11/2004 |
| WO | WO-2004/103954 A1 | 12/2004 |
| WO | WO-2004/108133 A2 | 12/2004 |
| WO | WO-05032493 A2 | 4/2005 |
| WO | WO-2005/0107460 A1 | 11/2005 |
| WO | WO-2006/048249 A1 | 5/2006 |
| WO | WO-2006/053227 A2 | 5/2006 |
| WO | WO-2006/066173 A2 | 6/2006 |
| WO | WO-2006/066174 A1 | 6/2006 |
| WO | WO-2006/066795 A1 | 6/2006 |
| WO | WO-2007/058626 A1 | 5/2007 |
| WO | WO-2007/095124 A2 | 8/2007 |
| WO | WO-2007/112914 A2 | 10/2007 |
| WO | WO-2007/117465 A2 | 10/2007 |
| WO | WO-2007/121154 A2 | 10/2007 |
| WO | WO-2008/030579 A2 | 3/2008 |
| WO | WO-2008/030584 A2 | 3/2008 |
| WO | WO-2008/061109 A2 | 5/2008 |
| WO | WO-2008073825 A1 | 6/2008 |
| WO | WO-2009/012312 A1 | 1/2009 |
| WO | WO-2009/019167 A1 | 2/2009 |
| WO | WO-2009/102468 A1 | 8/2009 |
| WO | WO-2010/071819 A1 | 6/2010 |
| WO | WO-2011/046954 A1 | 4/2011 |
| WO | WO-2011/133750 A1 | 10/2011 |
| WO | WO-2011/137219 A1 | 11/2011 |
| WO | WO-2011/163640 A1 | 12/2011 |
| WO | WO-2012007375 A1 | 1/2012 |

(Continued)

OTHER PUBLICATIONS

Balasubramanian et al. in Cancer Research Abstract 75(15 Suppl):Abstract nr 3646 (2015) (Year: 2015).*
Gerecitano et al. in Blood 126(23):254 (2015) (Year: 2015).*
L Li et al. in Leukemia 29, 1702-1712 (2015) (Year: 2015).*
Z Li et al. in Journal of Clinical Investigation 125(3):1081-1097 (2015) (Year: 2015).*
International Search Report and Written Opinion for International Application No. PCT/US/2018/058194 dated Feb. 3, 2019.
STN Registry database entry: [online] 2011, CAS RN 1301085-08-4 (Search date: Feb. 9, 2019).
STN Registry database entry: [online] 2011, CAS RN 1421459-19-9 (Search date: Feb. 9, 2019).
STN Registry database entry: [online] 2011, CAS RN 1421491-68-0 (Search date: Feb. 9, 2019).
STN Registry database entry: [online] 2011, CAS RN 1421497-05-3 (Search date: Feb. 9, 2019).

(Continued)

Primary Examiner — Dennis Heyer
(74) Attorney, Agent, or Firm — Foley Hoag LLP; David P. Halstead; Alexander J. Chatterley

(57) ABSTRACT

The present invention provides methods of treating hematological disorders and solid malignant tumors, using substituted indazole compounds and pharmaceutically acceptable salts thereof. The compounds inhibit IRAK4 and BCL-2 kinases.

7 Claims, 5 Drawing Sheets

(56) References Cited

FOREIGN PATENT DOCUMENTS

| | | | |
|---|---|---|---|
| WO | WO-2012/068546 A1 | 5/2012 | |
| WO | WO-2012/084704 A1 | 6/2012 | |
| WO | WO-2012/142125 A2 | 10/2012 | |
| WO | WO-2013/042137 A1 | 3/2013 | |
| WO | WO-2013/059587 A1 | 4/2013 | |
| WO | WO-2013/068458 A1 | 5/2013 | |
| WO | WO-2014/003483 A1 | 1/2014 | |
| WO | WO-2014/011902 A1 | 1/2014 | |
| WO | WO-2014/070979 A1 | 5/2014 | |
| WO | WO-2015/038503 A1 | 3/2015 | |
| WO | WO-2015/091426 A1 | 6/2015 | |
| WO | WO-2015/104662 A1 | 7/2015 | |
| WO | WO 2015/104688 | * | 7/2015 |
| WO | WO-2015/104688 A1 | 7/2015 | |
| WO | WO-2015/119998 A1 | 8/2015 | |
| WO | WO-2015/193846 A1 | 12/2015 | |
| WO | WO-2017/009798 A1 | 1/2017 | |
| WO | WO-2017/009806 A1 | 1/2017 | |
| WO | WO-2017/023941 A1 | 2/2017 | |
| WO | WO-2018/081738 A1 | 5/2018 | |

OTHER PUBLICATIONS

STN Registry database entry: [online] 2014, CAS RN 1178067-91-8 (Search date: Feb. 9, 2019).
STN Registry database entry: [online] 2014, CAS RN 1184469-61-1 (Search date: Feb. 9, 2019).
STN Registry database entry: [online] 2014, CAS RN 1223638-97-8 (Search date: Feb. 9, 2019).
STN Registry database entry: [online] 2014, CAS RN 1252319-44-0 (Search date: Feb. 9, 2019).
STN Registry database entry: [online] 2014, CAS RN 1274105-18-8 (Search date: Feb. 9, 2019).
STN Registry database entry: [online] 2014, CAS RN 1282974-67-7 (Search date: Feb. 9, 2019).
STN Registry database entry: [online] 2014, CAS RN 1333957-90-6 (Search date: Feb. 9, 2019).
STN Registry database entry: [online] 2014, CAS RN 1346410-97-6 (Search date: Feb. 9, 2019).
STN Registry database entry: [online] 2014, CAS RN 1367793-38-1 (Search date: Feb. 9, 2019).
STN Registry database entry: [online] 2014, CAS RN 1368333-88-3 (Search date: Feb. 9, 2019).
STN Registry database entry: [online] 2014, CAS RN 1369195-81-2 (Search date: Feb. 9, 2019).
STN Registry database entry: [online] 2014, CAS RN 1381262-66-3 (Search date: Feb. 9, 2019).
STN Registry database entry: [online] 2014, CAS RN 1381667-74-0 (Search date: Feb. 9, 2019).
STN Registry database entry: [online] 2014, CAS RN 1396710-33-0 (Search date: Feb. 9, 2019).
STN Registry database entry: [online] 2014, CAS RN 1405289-53-3 (Search date: Feb. 9, 2019).
STN Registry database entry: [online] 2014, CAS RN 1414842-47-9 (Search date: Feb. 9, 2019).
STN Registry database entry: [online] 2014, CAS RN 1414842-48-0 (Search date: Feb. 9, 2019).
STN Registry database entry: [online] 2014, CAS RN 1421504-43-9 (Search date: Feb. 9, 2019).
STN Registry database entry: [online] 2014, CAS RN 1421508-39-5 (Search date: Feb. 9, 2019).
STN Registry database entry: [online] 2014, CAS RN 1423498-44-5 (Search date: Feb. 9, 2019).
STN Registry database entry: [online] 2014, CAS RN 1522249-43-9 (Search date: Feb. 9, 2019).
STN Registry database entry: [online] 2014, CAS RN 1548563-20-7 (Search date: Feb. 9, 2019).
STN Registry database entry: [online] 2014, CAS RN 1570255-99-0 (Search date: Feb. 9, 2019).
STN Registry database entry: [online] 2014, CAS RN 1575185-05-5 (Search date: Feb. 9, 2019).
Takami et al., "Design and synthesis of Rho kinase inhibitors (I)," Bioorg Med Chem, 12:2115-2137 (2004).
Zhang et al., "Design, synthesis and evaluation of bicyclic benzamides as novel 5-HT1F receptor agonists," Bioorg Med Chem Lett, 14(24):6011-6016 (2004).
Alder, C. M. et al., "Identification of a Novel and Selective Series of Itk Inhibitors via a Template-Hopping Strategy", *Med. Chem. Lett.*, 4:948-952 (American Chemical Society, 2013).
Chen et al., "Design and Synthesis of a Series of Non-Peptide High-Affinity Human Corticotropin-Releasing Factor1 Receptor Antagonists," J Med Chem, 39:4358-4360 (1996).
Das et al., "Effects of Positional and Geometrical isomerism on the Biological Activity of Some Novel Oxazolidinones," Bioorg Med Chem Lett, 15:337-343 (2005).
Ex Parte Cao, Decision rendered by the Board of Patent Appeals and Interferences in U.S. Appl. No. 10/696,862 on Sep. 21, 2011.
Extended European Search Report issued by the European Patent Office in corresponding Application No. PCT/IB2015054620 dated Jan. 16, 2018.
Extended European Search Report issued by the European Patent Office in corresponding International Application No. PCT/IB2015/050217, dated May 2, 2017.
Extended European Search Report received for EP Patent Application No. 16823968, dated Dec. 10, 2018.
International Search Report and Written Opinion for International Application No. PCT/IB2016/054203 dated Sep. 23, 2016.
International Search Report from parent PCT application PCT/IB2015/050217 dated Apr. 29, 2015.
International Search Report from parent PCT application PCT/IB2015/054620 dated Oct. 19, 2015.
International Search Report from published parent PCT application PCT/IB2015/050119 dated Mar. 19, 2015.
STN Registry database entry: CAS RN 1181327-83-2 (Entered STN: Sep. 8, 2009). (Year: 2009).
STN Registry database entry: CAS RN 1301085-08-4 (Entered STN: May 26, 2011). (Year: 2011).
Sun et al., "Synthesis, in Vitro Evaluation and Cocrystal Structure of 4-Oxo-[1]benzopyrano[4,3-c]pyrazole Cryptosporidium parvum Inosine 5'-Monophosphate Dehydrogenase (CpIMPDH) Inhibitors," J Med Chem, 57:10544-10550 (2014).
Wang et al., "Crystal Structures of IRAK-4 Kinase in Complex with Inhibitors: A Serine/Threonine Kinase with Tyrosine as a Gatekeeper," Structure 14, 1835-1844 (2006).
Extended European Search Report issued by the European Patent Office in corresponding Application No. EP 16823970 dated Jun. 25, 2019.
Extended European Search Report issued by the European Patent Office in corresponding Application No. EP 18190333 dated Mar. 13, 2019.
International Search Report and Written Opinion for International Application No. PCT/IB2016/054229 dated Nov. 15, 2016.
Partial Search Report and Written Opinion for EP Patent Application No. EP16823970, dated Mar. 19, 2019.

* cited by examiner

COMPOUNDS AND COMPOSITIONS FOR TREATING HEMATOLOGICAL DISORDERS

RELATED APPLICATIONS

This application claims the benefit of priority to U.S. Provisional Patent Application Ser. No. 62/579,502, filed Oct. 31, 2017, the contents of which are hereby incorporated by reference herein in their entirety.

BACKGROUND

Diffuse large B-cell lymphoma (hereafter also referred to as "DLBCL") is an aggressive lymphoma that can arise in lymph nodes or outside of the lymphatic system, in the gastrointestinal tract, testes, thyroid, skin, breast, bone, or brain. DLBCL is a cancer of B cells, a type of white blood cell responsible for producing antibodies. It is the most common type of non-Hodgkin's lymphoma among adults, with an annual incidence of 7-8 cases per 100,000 people per year. This cancer occurs primarily in older individuals, with a median age of diagnosis at approximately 70 years of age, though it can also occur in children and young adults in rare cases. DLBCL is an aggressive tumor and the first sign of this illness is typically the observation of a rapidly growing mass. The five-year survival rate is only 58%.

DLBCL has subtypes that are named according to their cell of origin and include germinal center B-cell-like (GCB) and activated B-cell-like (ABC). They differ in having a worse prognosis and, in some cases, requiring particularized approaches to treatment.

In addition, Waldenstrom's macroglobulinemia (WM) is a non-Hodgkin's lymphoma that affects two types of B cells, lymphoplasmacytoid cells and plasma cells. WM is characterized by having high levels of a circulating antibody, immunoglobulin M (IgM), which is made and secreted by the cells involved in the disease. WM is a rare disease, with only about 1,500 cases per year in the United States. There is no single accepted treatment for WM and a marked variation in clinical outcome due to gaps in knowledge of the disease's molecular basis. Objective response rates are high (>80%) but complete response rates are low (0-15%).

Other types of non-Hodgkin's lymphoma include mantle cell lymphoma (MCL), marginal zone lymphoma (MZL), follicular lymphoma (FL), chronic lymphocytic leukemia (CLL), small lymphocytic lymphoma (SLL), CNS lymphoma, and testicular lymphoma. Non-Hodgkin's lymphoma can be caused by a variety of factors such as infections agents (Epstein-Barr virus, hepatitis C virus and human T-Cell leukemia virus), radiation and chemotherapy treatments, and autoimmune diseases. As a group, non-Hodgkin's lymphoma affects 2.1% of the US population during their life. The percentage of people who survive beyond five years after diagnosis is 71%.

In addition, myeloproliferative neoplasms (MPN) include myelodysplastic syndrome (MDS) and acute myeloid leukemia (AML). These cancers arise from precursors of the myeloid lineages in the bone marrow. Additional types of MPN include chronic myelogenous leukemia (CML), chronic neutrophilic leukemia (CNL), polycythemia vera, primary myelofibrosis, essential thrombocythemia, chronic eosinophilic leukemia, and mastocytosis. While investigational drug therapies have been developed, reliable cures are lacking.

A solid tumor is an abnormal mass of tissue that usually does not contain cysts or liquid areas. Solid tumors may be benign or malignant. Solid tumors are typically named for the type of cells that form them. Sarcomas, carcinomas, melanomas, and glioblastomas are the main types of solid malignant tumor. Sarcomas are tumors in a blood vessel, bone, fat tissue, ligament, lymph vessel, muscle or tendon. Carcinomas are tumors that form in epithelial cells. Epithelial cells are found in the skin, glands and the linings of organs, such as the bladder, ureters and parts of the kidney. Solid tumors have a range of treatments and prognoses depending on the type of cancer and characteristics of the patient (e.g., age, gender, genetic factors, environmental factors, other diseases or disorders, etc.).

Accordingly, there is a need for new treatments for cancer.

SUMMARY

Provided herein is a method of treating or preventing cancer in a subject, comprising administering to the subject a compound of Formula (I) conjointly with a B-cell lymphoma 2 (BCL-2) inhibitor:

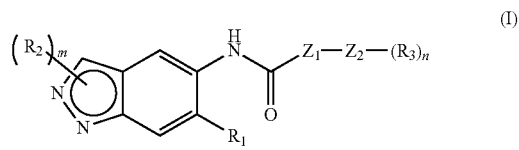

or a pharmaceutically acceptable salt thereof;
wherein,
$Z_1$ is an optionally substituted heteroaryl;
$Z_2$ is an optionally substituted heterocycloalkyl, optionally substituted heteroaryl or a direct bond;
$R_1$ is alkyl, cyano, —$NR_aR_b$, or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;
$R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
$R_3$, at each occurrence, independently is hydrogen, halogen, alkyl, haloalkyl, haloalkoxy, alkoxy, —$NR_aR_b$, hydroxyl or hydroxyalkyl;
$R_a$ is hydrogen or alkyl;
$R_b$ is hydrogen, alkyl, acyl, hydroxyalkyl, —$SO_2$-alkyl or optionally substituted cycloalkyl; and
'm' and 'n' are independently 1 or 2.

Provided herein is a method of treating or preventing cancer in a subject, comprising administering to the subject a compound of Formula (II) conjointly with a B-cell lymphoma 2 (BCL-2) inhibitor:

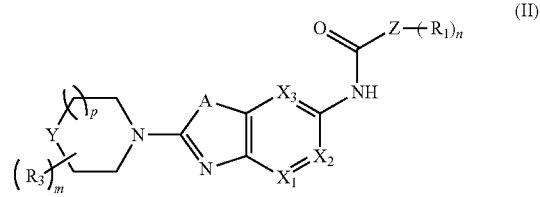

or a pharmaceutically acceptable salt thereof;
wherein, $X_1$ and $X_3$ independently are CH or N; $X_2$ is $CR_2$ or N; provided one and not more than one of $X_1$, $X_2$ or $X_3$ is N;

A is O or S;

Y is —$CH_2$— or O;

Z is aryl or heterocyclyl;

$R_1$, at each occurrence, is independently halo or optionally substituted heterocyclyl; wherein the substituent is alkyl, alkoxy, aminoalkyl, halo, hydroxyl, hydroxyalkyl or —$NR_aR_b$;

$R_2$ is hydrogen, optionally substituted cycloalkyl, optionally substituted aryl, optionally substituted heterocyclyl or —$NR_aR_b$; wherein the substituent is alkyl, amino, halo or hydroxyl;

$R_3$, at each occurrence, is alkyl or hydroxyl;

$R_a$ and $R_b$ are independently hydrogen, alkyl, acyl or heterocyclyl;

'm' and 'n' are independently 0, 1 or 2; and

'p' is 0 or 1.

Provided herein is a method of treating or preventing cancer in a subject, comprising administering to the subject a compound of Formula (III) conjointly with a B-cell lymphoma 2 (BCL-2) inhibitor:

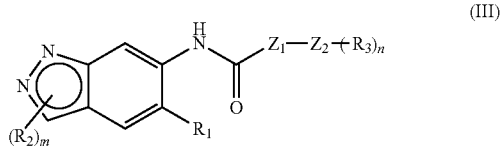

(III)

or a pharmaceutically acceptable salt thereof;
wherein, $Z_1$ is optionally substituted cycloalkyl, optionally substituted aryl, optionally substituted heterocyclyl or is absent;

$Z_2$ is optionally substituted cycloalkyl, optionally substituted aryl or optionally substituted heterocyclyl;

$R_1$ is hydrogen, optionally substituted alkyl, amino, halo, cyano, optionally substituted cycloalkyl, optionally substituted aryl, optionally substituted heterocyclyl, optionally substituted arylalkyl or optionally substituted heterocyclylalkyl;

$R_2$ at each occurrence is amino, optionally substituted alkyl, optionally substituted cycloalkyl, optionally substituted aryl, optionally substituted heterocyclyl, optionally substituted arylalkyl or optionally substituted heterocyclylalkyl;

$R_3$ at each occurrence is hydroxy, halo, optionally substituted alkyl, optionally substituted alkoxy, optionally substituted cycloalkyl or —$NR_aR_b$;

$R_a$ and $R_b$, independently for each occurrence, are hydrogen, optionally substituted alkyl, optionally substituted acyl, optionally substituted cycloalkyl, optionally substituted aryl, optionally substituted heterocyclyl, optionally substituted arylalkyl or optionally substituted heterocyclylalkyl;

m, at each occurrence, is 0, 1 or 2; and n, at each occurrence, is 0, 1, or 2.

In some embodiments, disclosed herein is a use of a compound disclosed herein or a pharmaceutically acceptable salt or a stereoisomer thereof together with an inhibitor of BCL-2 for the treatment and prevention of cancer.

In some embodiments, disclosed herein is a use of compound disclosed herein or a pharmaceutically acceptable salt or a stereoisomer thereof, including mixtures thereof in all ratios, as a medicament for treating cancer conjointly with an inhibitor of BCL-2.

In some embodiments, the cancer is non-Hodgkin's lymphoma selected from DLBCL, WM, MCL, MZL, FL, CLL, SLL, CNS lymphoma and testicular lymphoma. In some embodiments, the non-Hodgkin's lymphoma is DLBCL or WM.

In other embodiments, the cancer is a myeloproliferative neoplasm selected from MDS, AML, CML, CNL, polycythemia vera, primary myelofibrosis, essential thrombocythemia, chronic eosinophilic leukemia, and mastocytosis. In some embodiments, the myeloproliferative neoplasm is MDS or AML.

In some embodiments, the cancer is a solid malignant tumor, such as pancreatic cancer or breast cancer.

DETAILED DESCRIPTION

Figure 1:
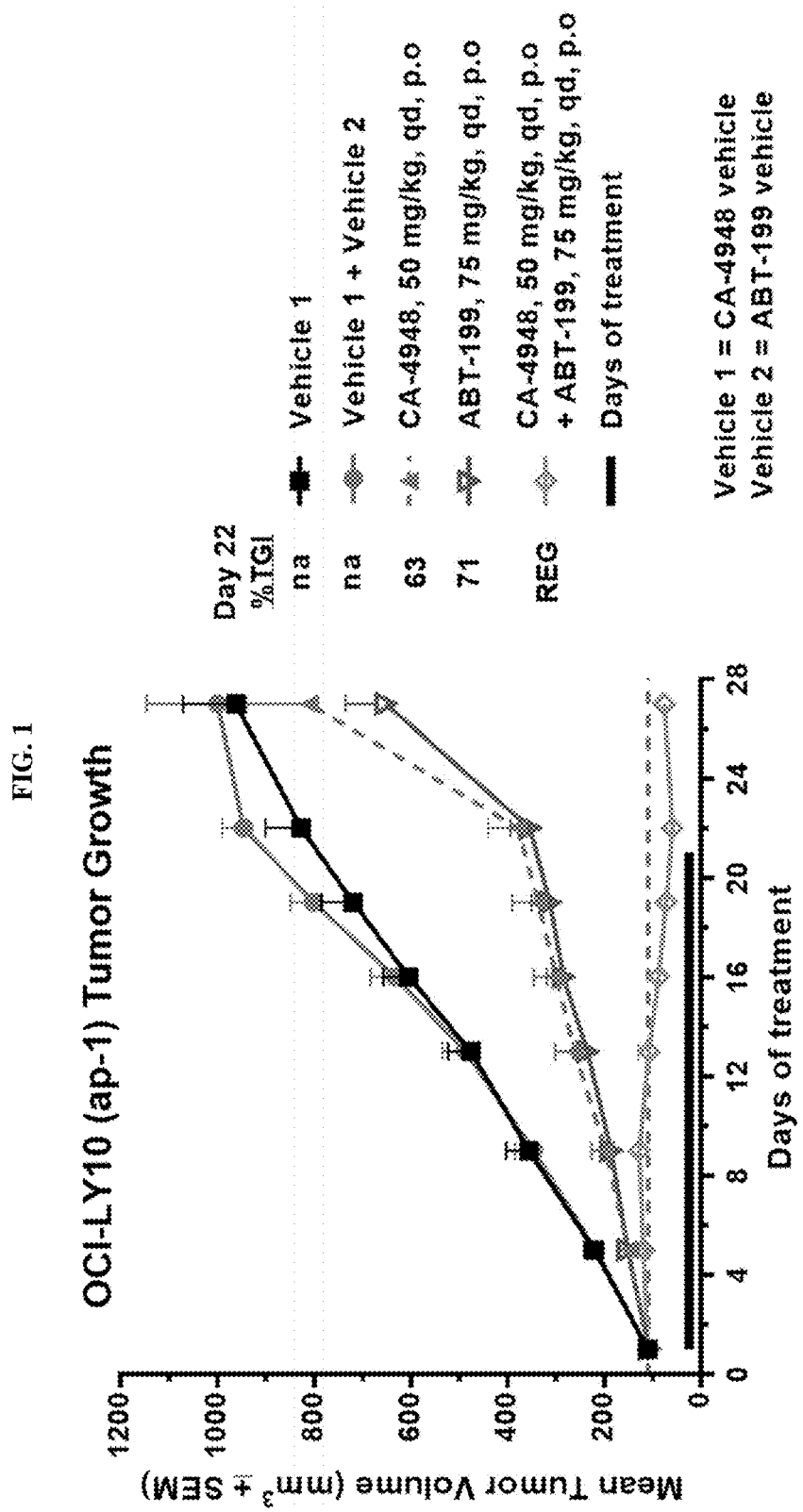
FIG. 1 shows the tumor growth response in three groups of tumor-bearing mice that had been treated with Compound A, venetoclax or a combination thereof, after 21 days.

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, alkoxyalkyl, halogen, alkyl, aryl, aryloxy, aralkyl, heteroaryl, heteroaryloxy, heteroaralkyl, cycloalkyl, cycloalkoxy, (cycloalkyl)alkyl, heterocyclyl, (heterocyclyl)alkyl, amino, aminoalkyl, alkylamino, dialkylamino, acyl, —C(O)$_2$H, —O(acyl), —NH(acyl), —N(alkyl)(acyl), cyano, phosphinate, phosphate, phosphonate, sulfonate, sulonamido, sulfate, haloalkyl or haloalkoxy. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to saturated aliphatic groups, including but not limited to C$_1$-C$_{10}$ straight-chain alkyl groups or C$_1$-C$_{10}$ branched-chain alkyl groups. Preferably, the "alkyl" group refers to C$_1$-C$_6$ straight-chain alkyl groups or C$_1$-C$_6$ branched-chain alkyl groups. Most preferably, the "alkyl" group refers to C$_1$-C$_4$ straight-chain alkyl groups or C$_1$-C$_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" refers to a group R—CO— wherein R is an optionally substituted alkyl group defined above. Examples of 'acyl' groups are, but not limited to, CH$_3$CO—, CH$_3$CH$_2$CO—, CH$_3$CH$_2$CH$_2$CO— or (CH$_3$)$_2$CHCO—.

As used herein, the term "alkoxy" refers to a straight or branched, saturated aliphatic C$_1$-C$_{10}$ hydrocarbon radical bonded to an oxygen atom that is attached to a core structure. Preferably, alkoxy groups have one to six carbon atoms. Examples of alkoxy groups include but are not limited to methoxy, ethoxy, propoxy, isopropoxy, butoxy, isobutoxy, tert-butoxy, pentoxy, 3-methyl butoxy and the like.

As used herein, the term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two and more of the same or different halogen atoms respectively. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl and the like.

As used herein, the term "haloalkoxy" refers to radicals wherein one or more of the hydrogen atoms of the alkoxy group are substituted with one or more halogens. Representative examples of "haloalkoxy" groups include, but not limited to, difluoromethoxy (—OCHF$_2$), trifluoromethoxy (—OCF$_3$) or trifluoroethoxy (—OCH$_2$CF$_3$).

As used herein, the term "aryl" alone or in combination with other term(s) means a 6- to 10-membered carbocyclic aromatic system containing one or two rings wherein such rings may be fused. The term "fused" means that the second ring is attached or formed by having two adjacent atoms in common with the first ring. The term "fused" is equivalent to the term "condensed". Examples of aryl groups include but are not limited to phenyl, naphthyl or indanyl. Unless otherwise specified, all aryl groups described herein may be optionally substituted.

The terms "amine" and "amino" are art-recognized and refer to both unsubstituted and substituted amines and salts thereof, e.g., a moiety that can be represented by

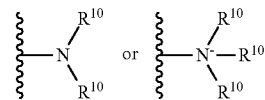

wherein each R$^{10}$ independently represents a hydrogen or a hydrocarbyl group, or two R$^{10}$ are taken together with the N atom to which they are attached complete a heterocycle having from 4 to 8 atoms in the ring structure.

As used herein, "aminoalkyl" refers to an amino group, as defined above, in which one or two hydrogen atoms are substituted with alkyl group.

As used herein, "nitro" refers to an —NO$_2$ group.

As used herein, "alkylamino" and "cycloalkylamino", refer to an —N-group, wherein nitrogen atom of said group being attached to alkyl or cycloalkyl respectively. Representative examples of an "Alkylamino" and "Cycloalkylamino" groups include, but are not limited to —NHCH$_3$ and —NH-cyclopropyl. An amino group can be optionally substituted with one or more of the suitable groups.

As used herein the term "cycloalkyl" alone or in combination with other term(s) means C$_3$-C$_{10}$ saturated cyclic hydrocarbon ring. A cycloalkyl may be a single ring, which typically contains from 3 to 7 carbon ring atoms. Examples of single-ring cycloalkyls include cyclopropyl, cyclobutyl, cyclopentyl, cyclohexyl, cycloheptyl and the like. A cycloalkyl may alternatively be polycyclic or contain more than one ring. Examples of polycyclic cycloalkyls include bridged, fused, and spirocyclic carbocyclyls.

As used herein, the term "cyano" refers to —CN group.

As used herein, the term "hydroxy" or "hydroxyl" refers to —OH group.

As used herein the term "hydroxyalkyl" or "hydroxylalkyl" means alkyl substituted with one or more hydroxyl groups, wherein the alkyl groups are as defined above. Examples of "hydroxyalkyl" include but are not limited to hydroxymethyl, hydroxyethyl, hydroxypropyl, propan-2-ol and the like.

As used herein, the term "halo" or "halogen" alone or in combination with other term(s) means fluorine, chlorine, bromine or iodine.

As used herein, the term "heterocyclyl" includes definitions of "heterocycloalkyl" and "heteroaryl".

As used herein, the term "heterocycloalkyl" refers to a non-aromatic, saturated or partially saturated, monocyclic or polycyclic ring system of 3 to 15 member having at least one heteroatom or heterogroup selected from O, N, S, S(O), S(O)$_2$, NH or C(O) with the remaining ring atoms being independently selected from carbon, oxygen, nitrogen, and sulfur. Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, 2-aza-bicyclo[2.2.2]octanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyland N-oxides thereof. More preferably, "heterocycloalkyl" includes azetidinyl, pyrrolidinyl, morpholinyl and piperidinyl. All heterocycloalkyl are optionally substituted by one or more aforesaid groups.

As used herein, the term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized or the N atom is optionally quarternized. Any suitable ring position of the heteroaryl moiety may be covalently linked to the defined chemical structure.

Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and the like.

Preferably "heteroaryl" refers to 5- to 6-membered ring selected from furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl and pyridazinyl. More preferably, pyrazolyl, pyridyl, oxazolyl and furanyl. All heteroaryls are optionally substituted by one or more aforesaid groups.

As used herein, the term 'compound(s)' comprises the compounds disclosed in the present invention.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

The phrase "pharmaceutically acceptable" refers to compounds or compositions that are physiologically tolerable and do not typically produce allergic or similar untoward reaction, including but not limited to gastric upset or dizziness when administered to mammal.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts, and the like. Certain compounds of the invention (can form pharmaceutically acceptable salts with various organic bases such as lysine, arginine, guanidine, diethanolamine or metformin. Suitable base salts include, but are not limited to, aluminum, calcium, lithium, magnesium, potassium, sodium, or zinc, salts.

As used herein, the term "stereoisomer" is a term used for all isomers of individual compounds of compound of formula (I) that differ only in the orientation of their atoms in space. The term stereoisomer includes mirror image isomers (enantiomers) of compounds of the present invention, mixtures of mirror image isomers (racemates, racemic mixtures) of compounds of the present invention, geometric (cis/trans or E/Z, R/S) isomers of compounds of the present invention and isomers of compounds of the present invention with more than one chiral center that are not mirror images of one another (diastereoisomers).

In certain embodiments, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses.

Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$. Isotopically labeled compounds of the present inventions can generally be prepared by following procedures well known in the art, such as by substituting an isotopically labeled reagent for a non-isotopically labeled reagent.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. The examples of carriers, stabilizers and adjuvant are mentioned in literature like, Martin, Remington's Pharmaceutical Sciences, 15th Ed., Mack Publ. Co., Easton, Pa. [1975].

The term "treatment"/"treating" means any treatment of a disease in a mammal, including: (a) Inhibiting the disease, i.e., slowing or arresting the development of clinical symptoms; and/or (b) Relieving the disease, i.e., causing the regression of clinical symptoms and/or (c) Alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" refers to an animal, preferably a mammal, and most preferably a human.

As used herein, the term, "therapeutically effective amount" refers to an amount of a compound of the present invention or a pharmaceutically acceptable salt or a stereoisomer thereof; or a composition comprising the compound of the present invention or a pharmaceutically acceptable salt or a stereoisomer thereof, effective in producing the desired therapeutic response in a particular patient suffering from AML. Particularly, the term "therapeutically effective amount" includes the amount of the compound of the present invention or a pharmaceutically acceptable salt or a stereoisomer thereof, when administered, that induces a positive modification in the disease or disorder to be treated or is sufficient to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. In some embodiments, the additional therapeutic compound is administered within about 5 minutes to within about 168 hours prior to or after administration of the compound of formula I, the compound of formula II, or the compound of formula III. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

Provided herein is a method of treating or preventing cancer in a subject, comprising administering to the subject a compound of Formula (I) conjointly with a B-cell lymphoma 2 (BCL-2) inhibitor:

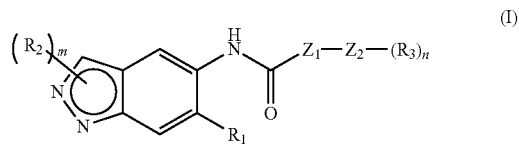

(I)

or a pharmaceutically acceptable salt thereof;
wherein
$Z_1$ is an optionally substituted heteroaryl;
$Z_2$ is an optionally substituted heterocycloalkyl, optionally substituted heteroaryl or a direct bond;
$R_1$ is alkyl, cyano, —$NR_aR_b$, or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;
$R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
$R_3$, at each occurrence, independently is hydrogen, halogen, alkyl, haloalkyl, haloalkoxy, alkoxy, —$NR_aR_b$, hydroxyl or hydroxyalkyl;
$R_a$ is hydrogen or alkyl;
$R_b$ is hydrogen, alkyl, acyl, hydroxyalkyl, —$SO_2$-alkyl or optionally substituted cycloalkyl; and
'm' and 'n' are independently 1 or 2.

In some embodiments, the present methods include a compound of formula (I) or a pharmaceutically acceptable salt thereof; wherein, $Z_1$ is a 5- or 6-membered optionally substituted heteroaryl.

In some embodiments, the present methods include a compound of formula (I) or a pharmaceutically acceptable salt thereof; wherein $Z_1$ is an optionally substituted heteroaryl; wherein the optional substituent is alkyl.

In some embodiments, the present methods include a compound of formula (I) or a pharmaceutically acceptable salt thereof, wherein $Z_1$ is selected from tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl and pyrazolyl.

In some embodiments, the present methods include a compound of formula (I) or a pharmaceutically acceptable salt thereof, wherein $Z_1$ is selected from pyridyl, oxazolyl and furanyl; wherein the pyridyl group is optionally substituted with alkyl; in particular alkyl is methyl.

In some embodiments, the present methods include a compound of formula (I) or a pharmaceutically acceptable salt thereof, wherein $Z_2$ is a 5- or 6-membered heteroaryl selected from tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl or pyrazolyl.

In some embodiments, the present methods include a compound of formula (I) or a pharmaceutically acceptable salt thereof, wherein $Z_2$ is a 5- or 6-membered heterocycloalkyl selected from azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl or 1,4-dioxanyl.

In some embodiments, the present methods include a compound of formula (I) or a pharmaceutically acceptable salt thereof, wherein $Z_2$ is pyridyl, pyrazolyl or pyrrolidinyl.

In some embodiments, the present methods include a compound of formula (I) or a pharmaceutically acceptable salt thereof, wherein $Z_2$ is a direct bond.

In some embodiments, the present methods include a compound of formula (I) that is a compound of formula (IA)

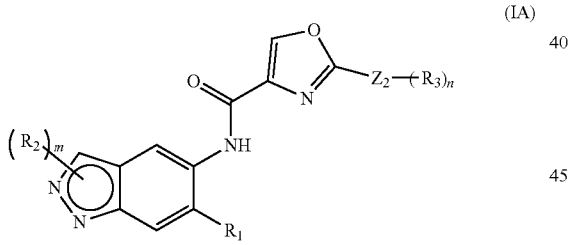

(IA)

or a pharmaceutically acceptable salt thereof;
wherein, $Z_2$, $R_1$, $R_2$, $R_3$, 'm' and 'n' are same as defined in compound of formula (I).

In some embodiments, the present methods include a compound of formula (I) that is a compound of formula (IB)

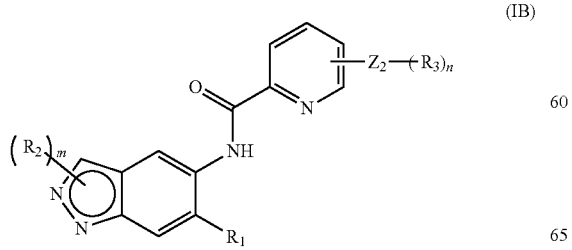

(IB)

or a pharmaceutically acceptable salt thereof;
wherein, $Z_2$, $R_1$, $R_2$, $R_3$, 'm' and 'n' are same as defined in compound of formula (I).

In some embodiments, the present methods include a compound of formula (I) that is a compound of formula (IC)

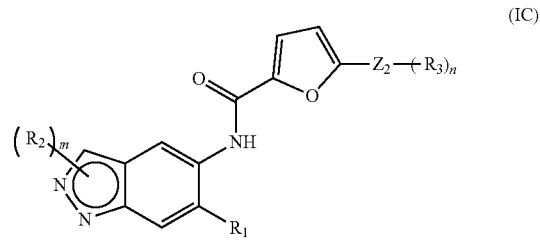

(IC)

or a pharmaceutically acceptable salt thereof;
wherein, $Z_2$, $R_1$, $R_2$, $R_3$, 'm' and 'n' are same as defined in compound of formula (I).

In some embodiments, the present methods include a compound of formula (I) wherein

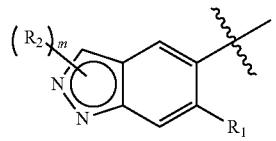

is

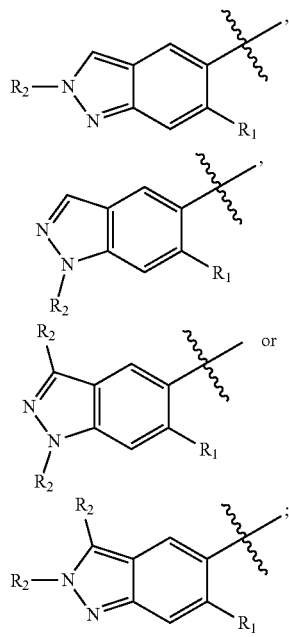

wherein $R_1$, $R_2$ and 'm' are same as defined in compound of formula (I).

In some embodiments, the present methods include a compound of formula (I) or a pharmaceutically acceptable salt thereof, wherein $Z_2$ is pyridyl.

In some embodiments, the present methods include a compound of formula (I) or a pharmaceutically acceptable salt thereof, wherein $Z_2$ is pyrazolyl.

In some embodiments, the present methods include a compound of formula (I) or a pharmaceutically acceptable salt thereof, wherein $Z_2$ is pyrrolidinyl.

In some embodiments, the present methods include a compound of formula (I) or a pharmaceutically acceptable salt thereof, wherein $R_1$ is optionally substituted heterocyclyl; wherein the substituent is halogen, hydroxyl, hydroxyalkyl, amino, aminoalkyl, —OCO—$CH_2$—O-alkyl, —OP(O)(O-alkyl)$_2$ or —$CH_2$—OP(O)(O-alkyl)$_2$.

In some embodiments, the present methods include a compound of formula (I) or a pharmaceutically acceptable salt thereof, wherein $R_1$ is optionally substituted azetidinyl, piperidinyl, morpholinyl, pyrrolidinyl or azepanyl; wherein the substituent is amino, halogen, hydroxyl, hydroxyalkyl, aminoalkyl, —OCO—$CH_2$—O-alkyl, —OP(O)(O-alkyl)$_2$ or —$CH_2$—OP(O)(O-alkyl)$_2$.

In some embodiments, the present methods include a compound of formula (I) or a pharmaceutically acceptable salt thereof, wherein $R_1$ is optionally substituted piperidinyl; wherein the substituent is hydroxyl.

In some embodiments, the present methods include a compound of formula (I) or a pharmaceutically acceptable salt thereof, wherein $R_1$ is optionally substituted phenyl; wherein the substituent is halogen.

In some embodiments, the present methods include a compound of formula (I) or a pharmaceutically acceptable salt thereof, wherein $R_1$ is cycloalkyl.

In some embodiments, the present methods include a compound of formula (I) or a pharmaceutically acceptable salt thereof, wherein $R_1$ is cyclopropyl or cyclohexyl.

In some embodiments, the present methods include a compound of formula (I) or a pharmaceutically acceptable salt thereof, wherein $R_1$ is —$NR_aR_b$; $R_a$ is hydrogen; $R_b$ is optionally substituted cycloalkyl; wherein the substituent is hydroxyl.

In some embodiments, the present methods include a compound of formula (I) or a pharmaceutically acceptable salt thereof, wherein $R_1$ is cyano.

In some embodiments, the present methods include a compound of formula (I) or a pharmaceutically acceptable salt thereof, wherein $R_2$ is optionally substituted alkyl; wherein substituent is alkoxy.

In some embodiments, the present methods include a compound of formula (I) or a pharmaceutically acceptable salt thereof, wherein $R_2$ is cycloalkyl.

In some embodiments, the present methods include a compound of formula (I) or a pharmaceutically acceptable salt thereof, wherein $R_3$ is hydrogen, halogen, alkyl, alkoxy, —$NR_aR_b$, hydroxyl or hydroxyalkyl; $R_a$ is hydrogen or alkyl; and $R_b$ is hydrogen, alkyl, acyl, hydroxyalkyl or —$SO_2$-alkyl.

In some embodiments, the present methods include a compound of formula (I) or a pharmaceutically acceptable salt thereof, wherein $Z_1$ is optionally substituted pyridyl; Ring $Z_2$ is pyridyl, pyrazolyl, pyrrolidinyl or direct bond; $R_1$ is an optionally substituted group selected from cyclopropyl, piperidinyl, morpholinyl or pyrrolidinyl; $R_2$ is optionally substituted alkyl or cycloalkyl; $R_3$ is hydrogen, halogen, alkyl, alkoxy, —$NR_aR_b$, hydroxyl or hydroxyalkyl; $R_a$ is hydrogen or alkyl; and $R_b$ is hydrogen or hydroxyalkyl.

In some embodiments, the present methods include a compound of formula (I) or a pharmaceutically acceptable salt thereof, wherein $Z_1$ is oxazolyl; $Z_2$ is pyridyl, pyrazolyl or pyrrolidinyl; $R_1$ is cyano, —$NR_aR_b$, or an optionally substituted group selected from cyclopropyl, cyclohexyl, phenyl, azetidinyl, piperidinyl, morpholinyl or pyrrolidinyl; $R_2$ is optionally substituted alkyl or cycloalkyl; $R_3$ is hydrogen, halogen, alkyl, alkoxy, —$NR_aR_b$, hydroxyl or hydroxyalkyl; $R_a$ is hydrogen or alkyl; and $R_b$ is hydrogen, alkyl, acyl, hydroxyalkyl, —$SO_2$-alkyl or optionally substituted cycloalkyl.

In some embodiments, the present methods include a s compound of formula (I) or a pharmaceutically acceptable salt thereof, wherein $R_3$ is —$NR_aR_b$; $R_a$ is hydrogen or alkyl; and $R_b$ is hydrogen, alkyl, acyl, hydroxyalkyl, —$SO_2$-alkyl or optionally substituted cycloalkyl; wherein the optional substituent is hydroxyl;

In some embodiments, the present methods include a compound of formula (I) or a pharmaceutically acceptable salt thereof, wherein 'n' is 1.

In some embodiments, the present methods include a compound of formula (I) or a pharmaceutically acceptable salt thereof, wherein 'n' is 2.

In some embodiments, the present methods include a compound of formula (I) or a pharmaceutically acceptable salt thereof, wherein 'm' is 1.

In some embodiments, the present methods include a compound of formula (I) or a pharmaceutically acceptable salt thereof, wherein 'm' is 2.

In some embodiments, the present methods include administering a compound of formula (I) selected from:

N-(2-methyl-6-(piperidin-1-yl)-2H-indazol-5-yl)-6-(1H-pyrazol-4-yl) picolinamide;

N-(2-methyl-6-(piperidin-1-yl)-2H-indazol-5-yl)-2-(2-methylpyridin-4-yl) oxazole-4-carboxamide;

N-(1-methyl-6-(piperidin-1-yl)-1H-indazol-5-yl)-2-(2-methylpyridin-4-yl) oxazole-4-carboxamide;

N-(2-cyclopentyl-6-(piperidin-1-yl)-2H-indazol-5-yl)-2-(2-methylpyridin-4-yl) oxazole-4-carboxamide;

N-(6-cyano-2-cyclopentyl-2H-indazol-5-yl)-2-(2-methyl-pyridin-4-yl) oxazole-4-carboxamide;

N-(2-cyclopentyl-6-cyclopropyl-2H-indazol-5-yl)-2-(2-methylpyridin-4-yl) oxazole-4-carboxamide;

N-(2-cyclopentyl-6-cyclopropyl-2H-indazol-5-yl)-6-(1H-pyrazol-4-yl) picolinamide;

N-(2-cyclopentyl-6-morpholino-2H-indazol-5-yl)-2-(2-methylpyridin-4-yl) oxazole-4-carboxamide;

6'-amino-N-(2-cyclopentyl-6-morpholino-2H-indazol-5-yl)-[2,3'-bipyridine]-6-carboxamide 2,2,2-trifluoroacetate;

N-(6-(3-fluorophenyl)-2-methyl-2H-indazol-5-yl)-2-(2-methylpyridin-4-yl)oxazole-4-carboxamide;

N-(6-cyclohexyl-2-methyl-2H-indazol-5-yl)-2-(2-methyl-pyridin-4-yl)oxazole-4-carboxamide hydrochloride;

6'-fluoro-N-(2-methyl-6-(piperidin-11-yl)-2H-indazol-5-yl)-[2,3'-bipyridine]-6-carboxamide hydrochloride;

N-(6-cyclohexyl-2-methyl-2H-indazol-5-yl)-6-(1H-pyrazol-4-yl)picolinamide hydrochloride;

2'-fluoro-N-(2-methyl-6-(piperidin-11-yl)-2H-indazol-5-yl)-[2,3'-bipyridine]-6-carboxamide;

2-(2-chloropyridin-4-yl)-N-(2-methyl-6-(piperidin-1-yl)-2H-indazol-5-yl)oxazole-4-carboxamide hydrochloride;

N-(6-cyclopropyl-2-methyl-2H-indazol-5-yl)-2-(2-methyl-pyridin-4-yl)oxazole-4-carboxamide hydrochloride;

N-(1-cyclopentyl-6-cyclopropyl-1H-indazol-5-yl)-6-(1-methyl-1H-pyrazol-4-yl)picolinamide;

N-(2-cyclopentyl-6-cyclopropyl-2H-indazol-5-yl)-6-(1-methyl-1H-pyrazol-4-yl)picolinamide;

6-(1-methyl-1H-pyrazol-4-yl)-N-(2-methyl-6-(piperidin-1-yl)-2H-indazol-5-yl)picolinamide;

N-(2-cyclopentyl-6-cyclopropyl-2H-indazol-5-yl)-2-(6-methoxypyridin-3-yl) oxazole-4-carboxamide;

2-(6-methoxypyridin-3-yl)-N-(2-methyl-6-(piperidin-1-yl)-2H-indazol-5-yl)oxazole-4-carboxamide;

N-(2-methyl-6-(piperidin-1-yl)-2H-indazol-5-yl)-2-(3-methylpyridin-4-yl)oxazole-4-carboxamide;
6-bromo-N-(2-methyl-6-(piperidin-1-yl)-2H-indazol-5-yl)picolinamide;
6-chloro-5-methyl-N-(2-methyl-6-(piperidin-1-yl)-2H-indazol-5-yl)picolinamide
N-(2-methyl-6-(piperidin-1-yl)-2H-indazol-5-yl)-2-(6-methylpyridin-3-yl)oxazole-4-carboxamide;
N-(2-cyclopentyl-6-cyclopropyl-2H-indazol-5-yl)-2-(2-methylpyridin-3-yl)oxazole-4-carboxamide;
N-(2-cyclopentyl-6-cyclopropyl-2H-indazol-5-yl)-2-(3-methylpyridin-4-yl)oxazole-4-carboxamide;
N-(2-cyclopentyl-6-cyclopropyl-2H-indazol-5-yl)-2-(6-methylpyridin-3-yl)oxazole-4-carboxamide;
6'-amino-3-methyl-N-(2-methyl-6-(piperidin-1-yl)-2H-indazol-5-yl)-[2,3'-bipyridine]-6-carboxamide hydrochloride;
5-methyl-6-(1-methyl-1H-pyrazol-4-yl)-N-(2-methyl-6-(piperidin-1-yl)-2H-indazol-5-yl)picolinamide;
N-(1-cyclopropyl-6-(piperidin-1-yl)-1H-indazol-5-yl)-2-(2-methylpyridin-4-yl)oxazole-4-carboxamide hydrochloride;
2-(2-hydroxypyridin-3-yl)-N-(2-methyl-6-(piperidin-1-yl)-2H-indazol-5-yl)oxazole-4-carboxamide;
(S)-6-(3-aminopyrrolidin-1-yl)-N-(2-methyl-6-(piperidin-1-yl)-2H-indazol-5-yl)picolinamide 2,2,2-trifluoroacetate;
(S)-6-(1-(2-hydroxypropyl)-1H-pyrazol-4-yl)-N-(2-methyl-6-(piperidin-1-yl)-2H-indazol-5-yl)picolinamide;
N-(1,6-dicyclopropyl-1H-indazol-5-yl)-2-(6-methoxypyridin-3-yl)oxazole-4-carboxamide;
N-(1,6-dicyclopropyl-1H-indazol-5-yl)-2-(2-methylpyridin-4-yl)oxazole-4-carboxamide hydrochloride;
(S)—N-(6-cyclopropyl-1-methyl-1H-indazol-5-yl)-6-(3-hydroxypyrrolidin-1-yl)picolinamide;
(R)-6-(3-hydroxypyrrolidin-1-yl)-N-(2-methyl-6-(piperidin-1-yl)-2H-indazol-5-yl)picolinamide;
(S)-6-(3-hydroxypyrrolidin-1-yl)-N-(2-methyl-6-(piperidin-1-yl)-2H-indazol-5-yl)picolinamide;
6-(3-hydroxypyrrolidin-1-yl)-N-(2-methyl-6-(piperidin-1-yl)-2H-indazol-5-yl)picolinamide;
(S)-6-(3-aminopyrrolidin-1-yl)-N-(6-cyclopropyl-1-methyl-1H-indazol-5-yl)picolinamide;
(R)-6-(3-aminopyrrolidin-1-yl)-N-(2-methyl-6-(piperidin-1-yl)-2H-indazol-5-yl)picolinamide;
(R)-6-(1-(2-hydroxypropyl)-1H-pyrazol-4-yl)-N-(2-methyl-6-(piperidin-1-yl)-2H-indazol-5-yl)picolinamide;
(S)-2-(3-aminopyrrolidin-1-yl)-N-(2-methyl-6-(piperidin-1-yl)-2H-indazol-5-yl)oxazole-4-carboxamide;
N-(6-cyclopropyl-1-methyl-1H-indazol-5-yl)-2-(2-methylpyridin-4-yl)oxazole-4-carboxamide;
(S)—N-(6-cyclopropyl-1-methyl-1H-indazol-5-yl)-6-(1-(2-hydroxypropyl)-1H-pyrazol-4-yl)picolinamide;
(S)—N-(6-cyclopropyl-2-methyl-2H-indazol-5-yl)-6-(1-(2-hydroxypropyl)-1H-pyrazol-4-yl)picolinamide;
(S)-6-(3-aminopyrrolidin-1-yl)-N-(6-cyclopropyl-2-methyl-2H-indazol-5-yl)picolinamide;
(S)—N-(6-cyclopropyl-2-methyl-2H-indazol-5-yl)-6-(3-hydroxypyrrolidin-1-yl)picolinamide;
(S)—N-(6-cyclopropyl-1-methyl-1H-indazol-5-yl)-2-(3-hydroxypyrrolidin-1-yl)oxazole-4-carboxamide;
(S)-2-(3-aminopyrrolidin-1-yl)-N-(6-cyclopropyl-1-methyl-1H-indazol-5-yl)oxazole-4-carboxamide;
(S)-2-(3-hydroxypyrrolidin-1-yl)-N-(2-methyl-6-(piperidin-1-yl)-2H-indazol-5-yl)oxazole-4-carboxamide;
(S)—N-(6-cyclopropyl-1-methyl-1H-indazol-5-yl)-2-(1-(2-hydroxypropyl)-1H-pyrazol-4-yl)oxazole-4-carboxamide;
(S)-2-(3-aminopyrrolidin-1-yl)-N-(6-cyclopropyl-2-methyl-2H-indazol-5-yl)oxazole-4-carboxamide;
(S)—N-(6-cyclopropyl-2-methyl-2H-indazol-5-yl)-2-(3-hydroxypyrrolidin-1-yl)oxazole-4-carboxamide;
(S)-6-(1-(2-hydroxypropyl)-1H-pyrazol-4-yl)-N-(2-methyl-6-(piperidin-1-yl)-2H-indazol-5-yl)picolinamide;
6-((2-hydroxypropyl)amino)-N-(2-methyl-6-(piperidin-1-yl)-2H-indazol-5-yl)picolinamide;
N-(6-(4-hydroxypiperidin-1-yl)-2-methyl-2H-indazol-5-yl)-2-(2-methylpyridin-4-yl)oxazole-4-carboxamide;
N-(6-(azetidin-1-yl)-1-methyl-1H-indazol-5-yl)-2-(2-methylpyridin-4-yl)oxazole-4-carboxamide;
N-(6-(azetidin-1-yl)-2-methyl-2H-indazol-5-yl)-2-(2-methylpyridin-4-yl)oxazole-4-carboxamide;
N-(6-(3-hydroxyazetidin-1-yl)-2-methyl-2H-indazol-5-yl)-2-(2-methylpyridin-4-yl)oxazole-4-carboxamide;
N-(1-methyl-6-(pyrrolidin-1-yl)-1H-indazol-5-yl)-2-(2-methylpyridin-4-yl)oxazole-4-carboxamide;
N-(2-methyl-6-(pyrrolidin-1-yl)-2H-indazol-5-yl)-2-(2-methylpyridin-4-yl)oxazole-4-carboxamide;
(S)—N-(6-(3-hydroxypyrrolidin-1-yl)-2-methyl-2H-indazol-5-yl)-2-(2-methylpyridin-4-yl)oxazole-4-carboxamide;
(R)—N-(6-(3-hydroxypyrrolidin-1-yl)-2-methyl-2H-indazol-5-yl)-2-(2-methylpyridin-4-yl)oxazole-4-carboxamide;
N-(2-methyl-6-(piperidin-1-yl)-2H-indazol-5-yl)-5-(2-methylpyridin-4-yl)furan-2-carboxamide;
N-(6-(4-hydroxypiperidin-1-yl)-2-methyl-2H-indazol-5-yl)-5-(2-methylpyridin-4-yl)furan-2-carboxamide;
N-(6-(3-hydroxypiperidin-1-yl)-2-methyl-2H-indazol-5-yl)-2-(2-methylpyridin-4-yl)oxazole-4-carboxamide;
(R)—N-(6-(3-hydroxypiperidin-1-yl)-2-methyl-2H-indazol-5-yl)-5-(2-methylpyridin-4-yl)furan-2-carboxamide;
N-(6-(3-hydroxypiperidin-1-yl)-2-methyl-2H-indazol-5-yl)-5-(2-methylpyridin-4-yl)furan-2-carboxamide;
N-(6-(azepan-1-yl)-2-methyl-2H-indazol-5-yl)-2-(2-methylpyridin-4-yl)oxazole-4-carboxamide;
N-(6-(azepan-1-yl)-1-methyl-1H-indazol-5-yl)-2-(2-methylpyridin-4-yl)oxazole-4-carboxamide;
N-(2,3-dimethyl-6-(piperidin-1-yl)-2H-indazol-5-yl)-2-(2-methylpyridin-4-yl)oxazole-4-carboxamide;
N-(1,3-dimethyl-6-(piperidin-1-yl)-1H-indazol-5-yl)-2-(2-methylpyridin-4-yl)oxazole-4-carboxamide;
N-(6-(4-hydroxypiperidin-1-yl)-1-(2-methoxyethyl)-1H-indazol-5-yl)-2-(2-methylpyridin-4-yl)oxazole-4-carboxamide;
N-(6-(4-hydroxypiperidin-1-yl)-2-(2-methoxyethyl)-2H-indazol-5-yl)-2-(2-methylpyridin-4-yl)oxazole-4-carboxamide;
N-(6-(4-hydroxypiperidin-1-yl)-1-methyl-1H-indazol-5-yl)-2-(2-methylpyridin-4-yl)oxazole-4-carboxamide;
N-(6-(4-fluoropiperidin-1l-yl)-1-methyl-1H-indazol-5-yl)-2-(2-methylpyridin-4-yl)oxazole-4-carboxamide;
N-(6-(3-fluoropiperidin-1-yl)-2-methyl-2H-indazol-5-yl)-2-(2-methylpyridin-4-yl)oxazole-4-carboxamide;
N-(6-(4-(hydroxymethyl)piperidin-1-yl)-2-methyl-2H-indazol-5-yl)-2-(2-methylpyridin-4-yl)oxazole-4-carboxamide;
N-(6-(4-hydroxypiperidin-1-yl)-1,3-dimethyl-1H-indazol-5-yl)-2-(2-methylpyridin-4-yl)oxazole-4-carboxamide;
N-(6-(3-(hydroxymethyl)piperidin-1-yl)-2-methyl-2-indazol-5-yl)-2-(2-methylpyridin-4-yl)oxazole-4-carboxamide;
N-(6-(4-hydroxypiperidin-1-yl)-2,3-dimethyl-2H-indazol-5-yl)-2-(2-methylpyridin-4-yl)oxazole-4-carboxamide;

2-(2-acetamidopyridin-4-yl)-N-(2-methyl-6-(piperidin-1-yl)-2H-indazol-5-yl)oxazole-4-carboxamide;
2-(2-acetamidopyridin-4-yl)-N-(6-(3-fluoropiperidin-1-yl)-2-methyl-2H-indazol-5-yl)oxazole-4-carboxamide;
2-(2-aminopyridin-4-yl)-N-(2-methyl-6-(piperidin-1-yl)-2H-indazol-5-yl)oxazole-4-carboxamide hydrochloride;
N-(6-(4-fluoropiperidin-1-yl)-1,3-dimethyl-1H-indazol-5-yl)-2-(2-methylpyridin-4-yl)oxazole-4-carboxamide;
N-(6-(((1R,4R)-4-hydroxycyclohexyl)amino)-2-methyl-2H-indazol-5-yl)-2-(2-methylpyridin-4-yl)oxazole-4-carboxamide;
N-(6-(4-(hydroxymethyl)piperidin-1-yl)-1-methyl-1H-indazol-5-yl)-2-(2-methylpyridin-4-yl)oxazole-4-carboxamide;
2-(2-aminopyridin-4-yl)-N-(6-(4-fluoropiperidin-1-yl)-2-methyl-2H-indazol-5-yl)oxazole-4-carboxamide hydrochloride;
N-(6-(4-fluoropiperidin-1-yl)-2-methyl-2H-indazol-5-yl)-2-(2-methylpyridin-4-yl)oxazole-4-carboxamide hydrochloride;
(S)—N-(6-(4-(hydroxymethyl)piperidin-1-yl)-2-methyl-2H-indazol-5-yl)-6-(1-(2-hydroxypropyl)-1H-pyrazol-4-yl)picolinamide;
2-(2-aminopyridin-4-yl)-N-(6-(4-hydroxypiperidin-1-yl)-2-methyl-2H-indazol-5-yl)oxazole-4-carboxamide hydrochloride;
N-(6-(4-(hydroxymethyl)piperidin-1-yl)-1-(2-methoxyethyl)-1H-indazol-5-yl)-2-(2-methylpyridin-4-yl)oxazole-4-carboxamide;
(S)—N-(6-(4-(hydroxymethyl)piperidin-1-yl)-1-methyl-1H-indazol-5-yl)-6-(1-(2-hydroxypropyl)-1H-pyrazol-4-yl)picolinamide;
N-(6-(4-(hydroxymethyl)piperidin-1-yl)-2-(2-methoxyethyl)-2H-indazol-5-yl)-2-(2-methylpyridin-4-yl)oxazole-4-carboxamide;
N-(6-(4-(hydroxymethyl)piperidin-1-yl)-2-methyl-2H-indazol-5-yl)-2-(2-methoxypyridin-4-yl)oxazole-4-carboxamide;
2-(2-acetamidopyridin-4-yl)-N-(6-(4-(hydroxymethyl)piperidin-1-yl)-2-methyl-2H-indazol-5-yl)oxazole-4-carboxamide;
2-(2-aminopyridin-4-yl)-N-(6-(4-(hydroxymethyl)piperidin-1-yl)-1-methyl-1H-indazol-5-yl)oxazole-4-carboxamide hydrochloride;
2-(2-aminopyridin-4-yl)-N-(6-(4-(hydroxymethyl)piperidin-1-yl)-2-methyl-2H-indazol-5-yl)oxazole-4-carboxamide hydrochloride;
N-(6-(4-hydroxypiperidin-1-yl)-1-methyl-1H-indazol-5-yl)-2-(2-methoxypyridin-4-yl)oxazole-4-carboxamide;
2-(2-aminopyridin-4-yl)-N-(6-(3-hydroxypiperidin-1-yl)-2-methyl-2H-indazol-5-yl)oxazole-4-carboxamide hydrochloride;
2-(2-methoxypyridin-4-yl)-N-(2-methyl-6-(piperidin-1-yl)-2H-indazol-5-yl)oxazole-4-carboxamide;
2-(2-aminopyridin-4-yl)-N-(6-(3-fluoropiperidin-1-yl)-2-methyl-2H-indazol-5-yl)oxazole-4-carboxamide hydrochloride;
(R)-2-(2-aminopyridin-4-yl)-N-(6-(3-hydroxypyrrolidin-1-yl)-2-methyl-2H-indazol-5-yl)oxazole-4-carboxamide hydrochloride;
1-(1,3-dimethyl-5-(2-(2-methylpyridin-4-yl)oxazole-4-carboxamido)-1H-indazol-6-yl)piperidin-4-yl 2-methoxyacetate;
N-(6-(4-hydroxypiperidin-1-yl)-2-methyl-2H-indazol-5-yl)-2-(2-methoxypyridin-4-yl)oxazole-4-carboxamide hydrochloride;
N-(6-(4-aminopiperidin-1-yl)-1-(2-methoxyethyl)-1H-indazol-5-yl)-2-(2-methylpyridin-4-yl)oxazole-4-carboxamide hydrochloride;
N-(6-(4-aminopiperidin-1-yl)-2-methyl-2H-indazol-5-yl)-2-(2-methylpyridin-4-yl)oxazole-4-carboxamide hydrochloride;
N-(6-(4-(hydroxymethyl)piperidin-1-yl)-1-(2-methoxyethyl)-3-methyl-1H-indazol-5-yl)-2-(2-methylpyridin-4-yl)oxazole-4-carboxamide;
N-(6-(4-(hydroxymethyl)piperidin-1-yl)-1,3-dimethyl-1H-indazol-5-yl)-2-(2-methylpyridin-4-yl)oxazole-4-carboxamide;
2-(2-aminopyridin-4-yl)-N-(6-(4-(hydroxymethyl)piperidin-1-yl)-1,3-dimethyl-1H-indazol-5-yl)oxazole-4-carboxamide;
N-(6-(4-hydroxypiperidin-1-yl)-1-methyl-1H-indazol-5-yl)-2-(2-hydroxypyridin-4-yl)oxazole-4-carboxamide;
2-(2,6-dimethylpyridin-4-yl)-N-(6-(4-hydroxypiperidin-1-yl)-1-methyl-1H-indazol-5-yl)oxazole-4-carboxamide;
(S)—N-(6-(3-hydroxypyrrolidin-1-yl)-1-methyl-1H-indazol-5-yl)-2-(2-methylpyridin-4-yl)oxazole-4-carboxamide;
N-(6-(4-hydroxypiperidin-1-yl)-1-(2-methoxyethyl)-3-methyl-1H-indazol-5-yl)-2-(2-methylpyridin-4-yl)oxazole-4-carboxamide;
N-(1-(2-hydroxyethyl)-6-(4-hydroxypiperidin-1-yl)-1H-indazol-5-yl)-2-(2-methylpyridin-4-yl)oxazole-4-carboxamide;
N-(6-(4-aminopiperidin-1-yl)-2-(2-methoxyethyl)-2H-indazol-5-yl)-2-(2-methylpyridin-4-yl)oxazole-4-carboxamide hydrochloride;
2-(2,6-dimethylpyridin-4-yl)-N-(2-methyl-6-(piperidin-1-yl)-2H-indazol-5-yl)oxazole-4-carboxamide hydrochloride;
2-(2-(dimethylamino)pyridin-4-yl)-N-(2-methyl-6-(piperidin-1-yl)-2H-indazol-5-yl)oxazole-4-carboxamide;
N-(6-(4-hydroxypiperidin-1-yl)-1-methyl-1H-indazol-5-yl)-2-(2-(methylamino)pyridin-4-yl)oxazole-4-carboxamide;
N-(2-methyl-6-(piperidin-1-yl)-2H-indazol-5-yl)-2-(2-(methylamino)pyridin-4-yl)oxazole-4-carboxamide;
N-(6-(4-hydroxypiperidin-1-yl)-2-methyl-2H-indazol-5-yl)-2-(2-(methylsulfonamido) pyridin-4-yl) oxazole-4-carboxamide;
2-(2-(dimethylamino) pyridin-4-yl)-N-(6-(4-hydroxypiperidin-1-yl)-1-methyl-1H-indazol-5-yl) oxazole-4-carboxamide;
N-(6-(4-(aminomethyl)piperidin-1-yl)-1-(2-methoxyethyl)-1H-indazol-5-yl)-2-(2-methylpyridin-4-yl)oxazole-4-carboxamide;
2-(2,6-dimethylpyridin-4-yl)-N-(6-(4-hydroxypiperidin-1-yl)-2-methyl-2H-indazol-5-yl) oxazole-4-carboxamide;
2-(2,6-dimethylpyridin-4-yl)-N-(6-(4-fluoropiperidin-1-yl)-2-methyl-2H-indazol-5-yl) oxazole-4-carboxamide;
Diethyl (1-(1-methyl-5-(2-(2-methylpyridin-4-yl)oxazole-4-carboxamido)-1H-indazol-6-yl)piperidin-4-yl) phosphate; and
Diethyl ((1-(2-methyl-5-(2-(2-methylpyridin-4-yl) oxazole-4-carboxamido)-2H-indazol-6-yl) piperidin-4-yl) methyl) phosphate;

or a pharmaceutically acceptable salt or a stereoisomer thereof.

In some embodiments, the compound of Formula (II) is Compound A.

Compound A

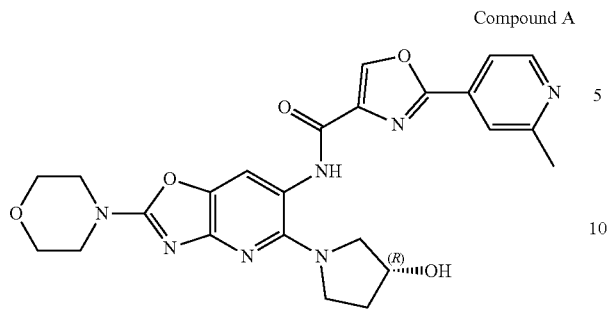

In some embodiments, the BCL-2 inhibitor is venetoclax.

Provided herein is a method of treating or preventing cancer in a subject, comprising administering to the subject a compound of Formula (II) conjointly with a B-cell lymphoma 2 (BCL-2) inhibitor:

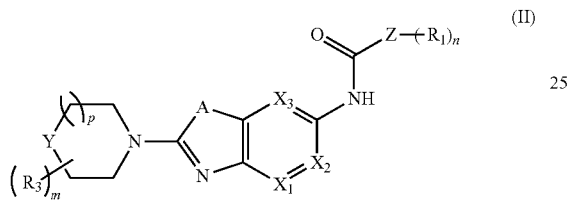

(II)

or a pharmaceutically acceptable salt thereof;
wherein, $X_1$ and $X_3$ independently are CH or N; $X_2$ is $CR_2$ or N; provided one and not more than one of $X_1$, $X_2$ or $X_3$ is N;

A is O or S;

Y is —CH$_2$— or O;

Z is aryl or heterocyclyl;

$R_1$, at each occurrence, is independently halo or optionally substituted heterocyclyl; wherein the substituent is alkyl, alkoxy, aminoalkyl, halo, hydroxyl, hydroxyalkyl or —NR$_a$R$_b$;

$R_2$ is hydrogen, optionally substituted cycloalkyl, optionally substituted aryl, optionally substituted heterocyclyl or —NR$_a$R$_b$; wherein the substituent is alkyl, amino, halo or hydroxyl;

$R_3$, at each occurrence, is alkyl or hydroxyl;

$R_a$ and $R_b$ are independently hydrogen, alkyl, acyl or heterocyclyl;

'm' and 'n' are independently 0, 1 or 2; and

'p' is 0 or 1.

In some embodiments, the present methods include a compound of formula (II) or a pharmaceutically acceptable salt thereof, wherein the group

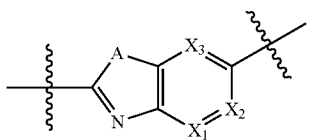

is

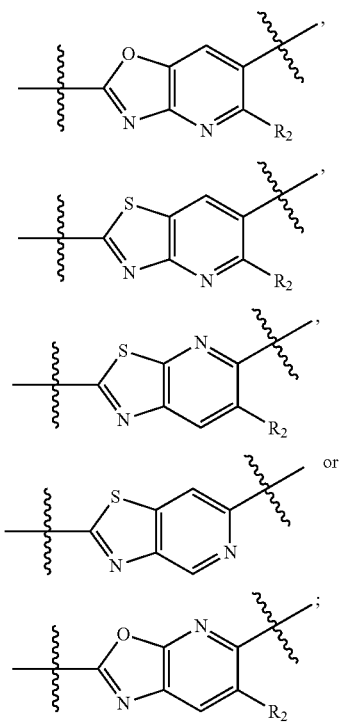

wherein $R_2$ are as defined in compound of formula (II).

In some embodiments, the present methods include a compound of formula (II) or a pharmaceutically acceptable salt thereof, wherein the Z is aryl or 5- or 6-membered heterocyclyl.

In some embodiments, the present methods include a compound of formula (II) or a pharmaceutically acceptable salt thereof, wherein the Z is phenyl, furanyl, thienyl, pyrrolyl, pyrazolyl, imidazolyl, oxazolyl, isoxazolyl, thiazolyl, isothiazolyl, 1H-tetrazolyl, oxadiazolyl, triazolyl, pyridyl, pyrimidinyl, pyrazinyl, pyridazinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl or dihydropyranyl; each of which is optionally substituted with alkyl, alkoxy, halo, hydroxyl, hydroxyalkyl or —NR$_a$R$_b$; $R_a$ and $R_b$ are independently are hydrogen, alkyl or acyl.

In some embodiments, the present methods include a compound of formula (II) or a pharmaceutically acceptable salt thereof, wherein Z is phenyl, oxazolyl, furanyl, thienyl or pyridyl; each of which is optionally substituted with one or more $R_1$.

In some embodiments, the present methods include a compound of formula (II) or a

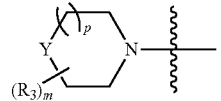

pharmaceutically acceptable salt thereof, wherein is

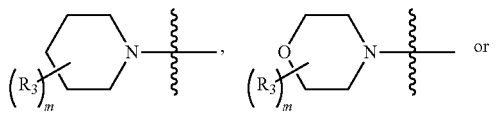

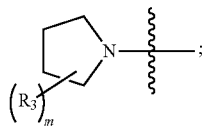

wherein R₃ and 'm' are defined in compound of formula (II).

In some embodiments, the present methods include a compound of formula (II) that is a compound of formula (IIA):

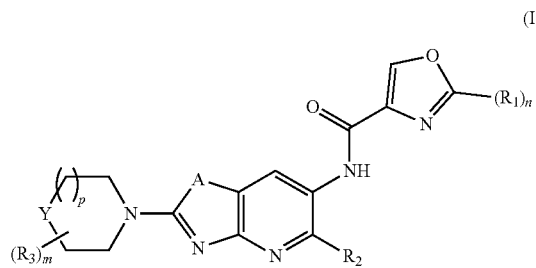

or a pharmaceutically acceptable salt thereof;
wherein, A, Y, $R_1$, $R_2$, $R_3$, 'm', 'p' and 'n' are same as defined in compound of formula (II).

In some embodiments, the present methods include a compound of formula (II) that is a compound of formula (IIB):

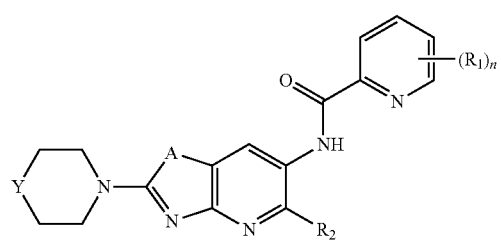

or a pharmaceutically acceptable salt thereof;
wherein, A, Y, $R_1$, $R_2$ and 'n' are same as defined in compound of formula (II).

In some embodiments, the present methods include a compound of formula (II) that is a compound of formula (IIC):

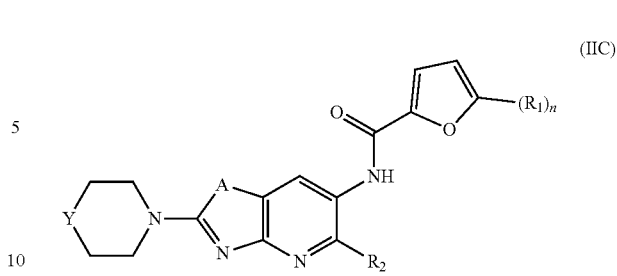

or a pharmaceutically acceptable salt thereof;
wherein, A, Y, $R_1$, $R_2$, $R_3$ and 'n' are same as defined compounds of formula (I).

In some embodiments, the present methods include a compound of formula (II), (IIA), (IIB), or (IIC) or a pharmaceutically acceptable salt thereof, wherein Y is O or $CH_2$.

In some embodiments, the present methods include a compound of formula (II) or a pharmaceutically acceptable salt thereof, wherein $R_1$ is optionally substituted heterocyclyl; wherein the substituent is alkyl, alkoxy, aminoalkyl, halo, hydroxyl, hydroxyalkyl or —$NR_aR_b$; $R_a$ and $R_b$ are independently hydrogen, alkyl or acyl.

In some embodiments, the present methods include a compound of formula (II) or a pharmaceutically acceptable salt thereof, wherein $R_1$ is pyridyl, pyrazolyl, pyrrolidinyl or piperidinyl; each of which is optionally substituted with alkyl, alkoxy, halo, hydroxyl, hydroxyalkyl or —$NR_aR_b$; $R_a$ and $R_b$ are independently hydrogen or acyl.

In some embodiments, the present methods include a compound of formula (II) or a pharmaceutically acceptable salt thereof, wherein $R_2$ is hydrogen.

In some embodiments, the present methods include a compound of formula (II) or a pharmaceutically acceptable salt thereof, wherein $R_2$ is optionally substituted cycloalkyl.

In some embodiments, the present methods include a compound of formula (II) or a pharmaceutically acceptable salt thereof, wherein $R_2$ is cyclopropyl.

In some embodiments, the present methods include a compound of formula (II) or a pharmaceutically acceptable salt thereof, wherein $R_2$ is optionally substituted heterocyclyl; wherein the substituent is alkyl, amino, halo or hydroxyl.

In some embodiments, the present methods include a compound of formula (II) or a pharmaceutically acceptable salt thereof, wherein $R_2$ is piperidinyl, pyrrolidinyl, morpholinyl, piperazinyl, azetidinyl, pyrazolyl, furanyl, pyridyl, azepanyl or azabicyclo[3.2.1]octanyl; wherein the substituent is alkyl, amino, halo or hydroxyl.

In some embodiments, the present methods include a compound of formula (II) or a pharmaceutically acceptable salt thereof, wherein $R_2$ is optionally substituted aryl; wherein the substituent is halo.

In some embodiments, the present methods include a compound of formula (II) or a pharmaceutically acceptable salt thereof, wherein $R_2$ is optionally substituted phenyl; wherein the substituent is fluoro.

In some embodiments, the present methods include a compound of formula (II) or a pharmaceutically acceptable salt thereof, wherein $R_2$ is —$NR_aR_b$; wherein $R_a$ and $R_b$ are independently hydrogen or heterocyclyl.

In some embodiments, the present methods include a compound of formula (II) or a pharmaceutically acceptable salt thereof, wherein $R_2$ is —$NR_aR_b$; wherein $R_a$ and $R_b$ are independently hydrogen or pyrrolidinyl.

In some embodiments, the present methods include a compound of formula (IIA) or a pharmaceutically acceptable salt thereof, wherein A is O or S; Y is —CH$_2$— or O; R$_1$ is halo, pyridyl, pyrazolyl, pyrrolidinyl each of which is optionally substituted with alkyl, alkoxy, halo, hydroxyl, hydroxyalkyl or —NR$_a$R$_b$; R$_2$ is hydrogen, optionally substituted cycloalkyl, optionally substituted aryl, optionally substituted heterocyclyl or —NR$_a$R$_b$; wherein the substituent is alkyl, amino, halo or hydroxyl; R$_a$ and R$_b$ are independently hydrogen or alkyl.

In some embodiments, the present methods include a compound of formula (IIB) or a pharmaceutically acceptable salt thereof, wherein A is O or S; Y is —CH$_2$— or O; R$_1$ is pyridyl, pyrazolyl, pyrrolidinyl; each of which is optionally substituted with alkyl, hydroxyl, hydroxyalkyl or —NR$_a$R$_b$; R$_a$ and R$_b$ are independently hydrogen; R$_2$ is hydrogen, optionally substituted cycloalkyl, optionally substituted aryl, optionally substituted heterocyclyl or —NR$_a$R$_b$; wherein the substituent is alkyl, amino, halo or hydroxyl; R$_a$ and R$_b$ are independently hydrogen, alkyl, acyl or heterocyclyl.

In some embodiments, the present methods include a compound of formula (IIA), (IIB) or (IIC), or a pharmaceutically acceptable salt thereof, wherein 'n' is 0, 1 or 2.

In some embodiments, the present methods include a compound of formula (IIA) or (IIB), or a pharmaceutically acceptable salt thereof, wherein 'p' is 0 or 1.

In some embodiments, the present methods include a compound of formula (IIA) or (IIB), or a pharmaceutically acceptable salt thereof, wherein 'm' is 0 or 2.

In some embodiments, the present methods include a compound of formula (II) selected from:

6'-amino-N-(2-morpholinooxazolo[4,5-b]pyridin-6-yl)-[2,3'-bipyridine]-6-carboxamide;
6'-amino-N-(5-cyclopropyl-2-morpholinooxazolo[4,5-b]pyridin-6-yl)-[2,3'-bipyridine]-6-carboxamide hydrochloride;
N-(5-cyclopropyl-2-morpholinooxazolo[4,5-b]pyridin-6-yl)-2-(2-methylpyridin-4-yl)oxazole-4-carboxamide hydrochloride;
N-(2,5-di(piperidin-1-yl)oxazolo[4,5-b]pyridin-6-yl)-6-(1H-pyrazol-4-yl)picolinamide hydrochloride;
N-(2,5-di(piperidin-1-yl)oxazolo[4,5-b]pyridin-6-yl)-2-(2-methylpyridin-4-yl)oxazole-4-carboxamide;
N-(2-morpholino-5-(piperidin-1-yl)oxazolo[4,5-b]pyridin-6-yl)-6-(1H-pyrazol-4-yl)picolinamide;
2-(2-methylpyridin-4-yl)-N-(2-morpholino-5-(piperidin-1-yl)oxazolo[4,5-b]pyridin-6-yl)oxazole-4-carboxamide;
6-chloro-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-6-(1-methyl-1H-pyrazol-4-yl)picolinamide;
2-(2-chloropyridin-4-yl)-N-(2,5-di(piperidin-1-yl)oxazolo[4,5-b]pyridin-6-yl)oxazole-4-carboxamide;
(S)-2-(2-methylpyridin-4-yl)-N-(2-morpholino-5-(pyrrolidin-3-ylamino)oxazolo[4,5-b]pyridin-6-yl)oxazole-4-carboxamide;
6'-amino-N-(2-morpholinooxazolo[5,4-b]pyridin-5-yl)-[2,3'-bipyridine]-6-carboxamide;
6'-amino-N-(2-morpholinothiazolo[4,5-c]pyridin-6-yl)-[2,3'-bipyridine]-6-carboxamide;
6'-amino-N-(2-morpholinothiazolo[5,4-b]pyridin-5-yl)-[2,3'-bipyridine]-6-carboxamide;
2-(2-methylpyridin-4-yl)-N-(2-morpholinothiazolo[4,5-b]pyridin-6-yl)oxazole-4-carboxamide;
6'-amino-N-(2-morpholinothiazolo[4,5-b]pyridin-6-yl)-[2,3'-bipyridine]-6-carboxamide;
N-(2-morpholinothiazolo[4,5-b]pyridin-6-yl)-6-(1H-pyrazol-4-yl)picolinamide;
3-(4-(aminomethyl)piperidin-1-yl)-5-fluoro-N-(2-morpholinothiazolo[4,5-b]pyridin-6-yl)benzamide;
2-(4-(aminomethyl)piperidin-1-yl)-5-fluoro-N-(2-morpholinothiazolo[4,5-b]pyridin-6-yl)benzamide;
2-(2-methylpyridin-4-yl)-N-(2-morpholino-5-(piperidin-1-yl)thiazolo[4,5-b]pyridin-6-yl)oxazole-4-carboxamide;
N-(2-morpholino-5-(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-2-(2-methylpyridin-4-yl)oxazole-4-carboxamide;
N-(2,5-dimorpholinooxazolo[4,5-b]pyridin-6-yl)-2-(2-methylpyridin-4-yl) oxazole-4-carboxamide;
N-(5-(4-methylpiperazin-1-yl)-2-morpholinooxazolo[4,5-b]pyridin-6-yl)-2-(2-methylpyridin-4-yl)oxazole-4-carboxamide;
N-(2,5-di(piperidin-1-yl)oxazolo[4,5-b]pyridin-6-yl)-2-(6-methoxypyridin-3-yl)oxazole-4-carboxamide;
N-(2,5-di(piperidin-1-yl)oxazolo[4,5-b]pyridin-6-yl)-2-(2-methylpyridin-3-yl)oxazole-4-carboxamide;
N-(2,5-di(piperidin-1-yl)oxazolo[4,5-b]pyridin-6-yl)-2-(2-hydroxypyridin-3-yl)oxazole-4-carboxamide;
2-(2-hydroxypyridin-3-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(6-hydroxypyridin-3-yl)oxazole-4-carboxamide;
2-(2-methoxypyridin-4-yl)-N-(2-morpholino-5-(piperidin-1-yl)oxazolo[4,5-b]pyridin-6-yl)oxazole-4-carboxamide;
2-(2-methylpyridin-3-yl)-N-(2-morpholino-5-(piperidin-1-yl)oxazolo[4,5-b]pyridin-6-yl)oxazole-4-carboxamide;
2-(3-methylpyridin-4-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(3-methylpyridin-4-yl)oxazole-4-carboxamide;
2-(6-methylpyridin-3-yl)-N-(2-morpholino-5-(piperidin-1-yl)oxazolo[4,5-b]pyridin-6-yl)oxazole-4-carboxamide;
6-(1-methyl-1H-pyrazol-4-yl)-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-2-(6-methylpyridin-3-yl)oxazole-4-carboxamide;
(S)—N-(5-(3-aminopyrrolidin-1-yl)-2-morpholinooxazolo[4,5-b]pyridin-6-yl)-2-(2-methylpyridin-4-yl)oxazole-4-carboxamide;
(S)—N-(5-(3-hydroxypyrrolidin-1-yl)-2-morpholinooxazolo[4,5-b]pyridin-6-yl)-2-(2-methylpyridin-4-yl)oxazole-4-carboxamide;
(R)—N-(5-(3-aminopyrrolidin-1-yl)-2-morpholinooxazolo[4,5-b]pyridin-6-yl)-2-(2-methylpyridin-4-yl)oxazole-4-carboxamide;
(R)—N-(5-(3-hydroxypyrrolidin-1-yl)-2-morpholinooxazolo[4,5-b]pyridin-6-yl)-2-(2-methylpyridin-4-yl)oxazole-4-carboxamide;
(S)-2-(3-aminopyrrolidin-1-yl)-N-(2-morpholino-5-(piperidin-1-yl)oxazolo[4,5-b]pyridin-6-yl)oxazole-4-carboxamide;
(S)-6-(3-hydroxypyrrolidin-1-yl)-N-(2-morpholino-5-(piperidin-1-yl)oxazolo[4,5-b]pyridin-6-yl)picolinamide;
(S)-6-(3-aminopyrrolidin-1-yl)-N-(2-morpholino-5-(piperidin-1-yl)oxazolo[4,5-b]pyridin-6-yl)picolinamide;
(S)-2-(3-hydroxypyrrolidin-1-yl)-N-(2-morpholino-5-(piperidin-1-yl)oxazolo[4,5-b]pyridin-6-yl)oxazole-4-carboxamide;

(S)—N-(5-cyclopropyl-2-morpholinooxazolo[4,5-b]pyridin-6-yl)-2-(3-hydroxypyrrolidin-1-yl)oxazole-4-carboxamide;

(S)-2-(3-aminopyrrolidin-1-yl)-N-(5-cyclopropyl-2-morpholinooxazolo[4,5-b]pyridin-6-yl)oxazole-4-carboxamide;

2-(2-methylpyridin-4-yl)-N-(5-(piperidin-1-yl)-2-(pyrrolidin-1-yl)oxazolo[4,5-b]pyridin-6-yl)oxazole-4-carboxamide hydrochloride;

N-(2-(2,6-dimethylmorpholino)-5-(piperidin-1-yl)oxazolo[4,5-b]pyridin-6-yl)-2-(2-methylpyridin-4-yl)oxazole-4-carboxamide hydrochloride;

N-(2,5-di(piperidin-1-yl)thiazolo[4,5-b]pyridin-6-yl)-6-(1-methyl-1H-pyrazol-4-yl)picolinamide hydrochloride;

6-(1-methyl-1H-pyrazol-4-yl)-N-(2-morpholino-5-(piperidin-1-yl)thiazolo[4,5-b]pyridin-6-yl)picolinamide;

N-(2,5-di(piperidin-1-yl)thiazolo[4,5-b]pyridin-6-yl)-2-(2-methylpyridin-3-yl)oxazole-4-carboxamide hydrochloride;

N-(2-((2S,6R)-2,6-dimethylmorpholino)-5-(piperidin-1-yl)thiazolo[4,5-b]pyridin-6-yl)-2-(2-methylpyridin-4-yl)oxazole-4-carboxamide;

2-(2-methylpyridin-3-yl)-N-(2-morpholino-5-(piperidin-1-yl)thiazolo[4,5-b]pyridin-6-yl)oxazole-4-carboxamide;

2-(2-hydroxypyridin-3-yl)-N-(2-morpholino-5-(piperidin-1-yl)thiazolo[4,5-b]pyridin-6-yl)oxazole-4-carboxamide;

N-(2,5-di(piperidin-1-yl)thiazolo[4,5-b]pyridin-6-yl)-2-(2-methoxypyridin-4-yl)oxazole-4-carboxamide;

2-(6-methoxypyridin-3-yl)-N-(2-morpholino-5-(piperidin-1-yl)thiazolo[4,5-b]pyridin-6-yl)oxazole-4-carboxamide;

2-(2-methoxypyridin-4-yl)-N-(2-morpholino-5-(piperidin-1-yl)thiazolo[4,5-b]pyridin-6-yl)oxazole-4-carboxamide;

(S)—N-(5-(3-fluoropiperidin-1-yl)-2-morpholinothiazolo[4,5-b]pyridin-6-yl)-2-(2-methylpyridin-4-yl)oxazole-4-carboxamide;

2-(6-methylpyridin-3-yl)-N-(2-morpholino-5-(piperidin-1-yl)thiazolo[4,5-b]pyridin-6-yl)oxazole-4-carboxamide;

2-(3-methylpyridin-4-yl)-N-(2-morpholino-5-(piperidin-1-yl)thiazolo[4,5-b]pyridin-6-yl)oxazole-4-carboxamide;

(S)-6-(3-aminopyrrolidin-1-yl)-N-(2-morpholino-5-(piperidin-1-yl)thiazolo[4,5-b]pyridin-6-yl)picolinamide;

(S)-6-(3-hydroxypyrrolidin-1-yl)-N-(2-morpholino-5-(piperidin-1-yl)thiazolo[4,5-b]pyridin-6-yl)picolinamide;

(S)-6-(3-aminopyrrolidin-1-yl)-N-(2,5-di(piperidin-1-yl)thiazolo[4,5-b]pyridin-6-yl)picolinamide;

(S)—N-(2,5-di(piperidin-1-yl)thiazolo[4,5-b]pyridin-6-yl)-6-(3-hydroxypyrrolidin-1-yl)picolinamide;

(S)-2-(3-aminopyrrolidin-1-yl)-N-(2-morpholino-5-(piperidin-1-yl)thiazolo[4,5-b]pyridin-6-yl)oxazole-4-carboxamide;

(S)—N-(5-(3-aminopyrrolidin-1-yl)-2-morpholinothiazolo[4,5-b]pyridin-6-yl)-2-(2-methylpyridin-4-yl)oxazole-4-carboxamide;

(S)-2-(3-aminopyrrolidin-1-yl)-N-(5-cyclopropyl-2-morpholinothiazolo[4,5-b]pyridin-6-yl)oxazole-4-carboxamide;

N-(5-cyclopropyl-2-morpholinothiazolo[4,5-b]pyridin-6-yl)-2-(2-methylpyridin-4-yl)oxazole-4-carboxamide;

(S)-2-(3-hydroxypyrrolidin-1-yl)-N-(2-morpholino-5-(piperidin-1-yl)thiazolo[4,5-b]pyridin-6-yl)oxazole-4-carboxamide;

(S)—N-(5-(3-hydroxypyrrolidin-1-yl)-2-morpholinothiazolo[4,5-b]pyridin-6-yl)-2-(2-methylpyridin-4-yl)oxazole-4-carboxamide;

(S)—N-(5-cyclopropyl-2-morpholinothiazolo[4,5-b]pyridin-6-yl)-6-(3-hydroxypyrrolidin-1-yl)picolinamide;

(S)—N-(5-cyclopropyl-2-morpholinothiazolo[4,5-b]pyridin-6-yl)-2-(3-hydroxypyrrolidin-1-yl)oxazole-4-carboxamide;

(S)—N-(5-cyclopropyl-2-morpholinothiazolo[4,5-b]pyridin-6-yl)-6-(1-(2-hydroxypropyl)-1H-pyrazol-4-yl)picolinamide;

(S)—N-(5-cyclopropyl-2-morpholinothiazolo[4,5-b]pyridin-6-yl)-2-(1-(2-hydroxypropyl)-1H-pyrazol-4-yl)oxazole-4-carboxamide;

N-(5-(3-hydroxypyrrolidin-1-yl)-2-morpholinothiazolo[4,5-b]pyridin-6-yl)-2-(6-methoxypyridin-3-yl)oxazole-4-carboxamide;

(S)—N-(5-(3-hydroxypyrrolidin-1-yl)-2-morpholinothiazolo[4,5-b]pyridin-6-yl)-2-(6-methoxypyridin-3-yl)oxazole-4-carboxamide;

(R)—N-(5-(3-hydroxypyrrolidin-1-yl)-2-morpholinothiazolo[4,5-b]pyridin-6-yl)-2-(6-methoxypyridin-3-yl)oxazole-4-carboxamide;

(S)—N-(5-(azetidin-1-yl)-2-morpholinothiazolo[4,5-b]pyridin-6-yl)-6-(3-hydroxypyrrolidin-1-yl)picolinamide;

N-(5-(3-hydroxyazetidin-1-yl)-2-morpholinothiazolo[4,5-b]pyridin-6-yl)-2-(2-methylpyridin-4-yl)oxazole-4-carboxamide;

(S)—N-(5-(3-hydroxypyrrolidin-1-yl)-2-morpholinothiazolo[4,5-b]pyridin-6-yl)-5-(2-methylpyridin-4-yl)thiophene-2-carboxamide;

(S)—N-(5-(3-hydroxypyrrolidin-1-yl)-2-morpholinothiazolo[4,5-b]pyridin-6-yl)-5-(2-methylpyridin-4-yl)furan-2-carboxamide;

(S)—N-(5-(3-hydroxypiperidin-1-yl)-2-morpholinothiazolo[4,5-b]pyridin-6-yl)-2-(2-methylpyridin-4-yl)oxazole-4-carboxamide;

N-(5-(4-hydroxypiperidin-1-yl)-2-morpholinothiazolo[4,5-b]pyridin-6-yl)-2-(2-methylpyridin-4-yl)oxazole-4-carboxamide (R)—N-(5-(3-hydroxypyrrolidin-1-yl)-2-morpholinothiazolo[4,5-b]pyridin-6-yl)-2-(2-methylpyridin-4-yl)oxazole-4-carboxamide;

N-(5-(4-hydroxypiperidin-1-yl)-2-morpholinothiazolo[4,5-b]pyridin-6-yl)-5-(2-methylpyridin-4-yl)furan-2-carboxamide;

N-(5-(azetidin-1-yl)-2-(piperidin-1-yl)thiazolo[4,5-b]pyridin-6-yl)-2-(2-methylpyridin-4-yl)oxazole-4-carboxamide;

2-(2-methylpyridin-4-yl)-N-(2-(piperidin-1-yl)-5-(pyrrolidin-1-yl)thiazolo[4,5-b]pyridin-6-yl)oxazole-4-carboxamide;

2-(2-methylpyridin-4-yl)-N-(2-morpholino-5-(pyrrolidin-1-yl)thiazolo[4,5-b]pyridin-6-yl)oxazole-4-carboxamide;

5-(2-methylpyridin-4-yl)-N-(2-morpholino-5-(piperidin-1-yl)thiazolo[4,5-b]pyridin-6-yl)furan-2-carboxamide;

N-(5-(azepan-1-yl)-2-morpholinothiazolo[4,5-b]pyridin-6-yl)-2-(2-methylpyridin-4-yl)oxazole-4-carboxamide;

2-(2-aminopyridin-4-yl)-N-(2-morpholino-5-(piperidin-1-yl)thiazolo[4,5-b]pyridin-6-yl)oxazole-4-carboxamide hydrochloride;

N-(5-(azetidin-1-yl)-2-morpholinothiazolo[4,5-b]pyridin-6-yl)-2-(2-methylpyridin-4-yl)oxazole-4-carboxamide;

(R)—N-(5-(3-hydroxypiperidin-1-yl)-2-morpholinothiazolo[4,5-b]pyridin-6-yl)-2-(2-methylpyridin-4-yl)oxazole-4-carboxamide;

(R)—N-(5-(3-hydroxypiperidin-1-yl)-2-morpholinothiazolo[4,5-b]pyridin-6-yl)-5-(2-methylpyridin-4-yl)furan-2-carboxamide;

(S)-6-(1-(2-hydroxypropyl)-1H-pyrazol-4-yl)-N-(2-morpholino-5-(piperidin-1-yl)thiazolo[4,5-b]pyridin-6-yl)picolinamide N-(5-(4-fluoropiperidin-1-yl)-2-morpholinothiazolo[4,5-b]pyridin-6-yl)-5-(2-methylpyridin-4-yl)furan-2-carboxamide N-(5-(4-fluoropiperidin-1-yl)-2-morpholinothiazolo[4,5-b]pyridin-6-yl)-2-(2-methylpyridin-4-yl)oxazole-4-carboxamide hydrochloride N-(5-(1-methyl-1H-pyrazol-4-yl)-2-morpholinothiazolo[4,5-b]pyridin-6-yl)-2-(2-methylpyridin-4-yl)oxazole-4-carboxamide;

N-(5-(3-fluorophenyl)-2-morpholinothiazolo[4,5-b]pyridin-6-yl)-2-(2-methylpyridin-4-yl)oxazole-4-carboxamide;

N-(5-(4-hydroxypiperidin-1-yl)-2-morpholinothiazolo[4,5-b]pyridin-6-yl)-5-(2-methylpyridin-4-yl)furan-2-carboxamide;

N-(5-(3-fluoropiperidin-1-yl)-2-morpholinothiazolo[4,5-b]pyridin-6-yl)-5-(2-methylpyridin-4-yl)furan-2-carboxamide;

(S)—N-(5-(3-hydroxypyrrolidin-1-yl)-2-morpholinooxazolo[4,5-b]pyridin-6-yl)-2-(6 methoxypyridin-3-yl)oxazole-4-carboxamide;

N-(5-(3-hydroxypyrrolidin-1-yl)-2-morpholinooxazolo[4,5-b]pyridin-6-yl)-2-(2-methylpyridin-4-yl)oxazole-4-carboxamide;

(R)—N-(5-(3-hydroxypyrrolidin-1-yl)-2-morpholinooxazolo[4,5-b]pyridin-6-yl)-2-(6 methoxypyridin-3-yl)oxazole-4-carboxamide;

N-(5-(3-hydroxypyrrolidin-1-yl)-2-morpholinooxazolo[4,5-b]pyridin-6-yl)-2-(6-methoxypyridin-3-yl)oxazole-4-carboxamide;

(S)—N-(5-(3-hydroxypyrrolidin-1-yl)-2-morpholinooxazolo[4,5-b]pyridin-6-yl)-5-(2-methylpyridin-4-yl)furan-2-carboxamide;

(S)—N-(5-(3-hydroxypyrrolidin-1-yl)-2-morpholinooxazolo[4,5-b]pyridin-6-yl)-5-(2-methylpyridin-4-yl)thiophene-2-carboxamide;

N-(5-(azetidin-1-yl)-2-(piperidin-1-yl)oxazolo[4,5-b]pyridin-6-yl)-2-(2-methylpyridin-4-yl)oxazole-4-carboxamide;

2-(2-methylpyridin-4-yl)-N-(2-(piperidin-1-yl)-5-(pyrrolidin-1-yl)oxazolo[4,5-b]pyridin-6-yl)oxazole-4-carboxamide;

5-(2-methylpyridin-4-yl)-N-(2-morpholino-5-(piperidin-1-yl)oxazolo[4,5-b]pyridin-6-yl)furan-2-carboxamide;

N-(5-(azetidin-1-yl)-2-morpholinooxazolo[4,5-b]pyridin-6-yl)-2-(2-methylpyridin-4-yl)oxazole-4-carboxamide;

2-(2-methylpyridin-4-yl)-N-(2-morpholino-5-(pyrrolidin-1-yl)oxazolo[4,5-b]pyridin-6-yl)oxazole-4-carboxamide;

N-(5-(4-hydroxypiperidin-1-yl)-2-morpholinooxazolo[4,5-b]pyridin-6-yl)-5-(2-methylpyridin-4-yl)furan-2-carboxamide;

(R)—N-(5-(3-hydroxypiperidin-1-yl)-2-morpholinooxazolo[4,5-b]pyridin-6-yl)-5-(2-methylpyridin-4-yl)furan-2-carboxamide;

N-(5-(furan-3-yl)-2-morpholinooxazolo[4,5-b]pyridin-6-yl)-2-(2-methylpyridin-4-yl)oxazole-4-carboxamide;

N-(5-(3-fluoropiperidin-1-yl)-2-morpholinooxazolo[4,5-b]pyridin-6-yl)-2-(2-methylpyridin-4-yl)oxazole-4-carboxamide;

N-(5-(4-hydroxypiperidin-1-yl)-2-morpholinooxazolo[4,5-b]pyridin-6-yl)-2-(2-methylpyridin-4-yl)oxazole-4-carboxamide;

N-(5-(4-fluoropiperidin-1-yl)-2-morpholinooxazolo[4,5-b]pyridin-6-yl)-2-(2-methylpyridin-4-yl)oxazole-4-carboxamide;

(S)—N-(5-(3-aminopiperidin-1-yl)-2-morpholinothiazolo[4,5-b]pyridin-6-yl)-2-(2-methylpyridin-4-yl)oxazole-4-carboxamide;

2-(2-methylpyridin-4-yl)-N-(2-morpholino-5-(1H-pyrazol-4-yl)thiazolo[4,5-b]pyridin-6-yl)oxazole-4-carboxamide;

N-(5-(6-fluoropyridin-3-yl)-2-morpholinothiazolo[4,5-b]pyridin-6-yl)-2-(2-methylpyridin-4-yl)oxazole-4-carboxamide;

N-(5-(3-hydroxy-8-azabicyclo[3.2.1]octan-8-yl)-2-morpholinothiazolo[4,5-b]pyridin-6-yl)-2-(2-methylpyridin-4-yl)oxazole-4-carboxamide;

N-(2-(3-hydroxypiperidin-1-yl)-5-(piperidin-1-yl)thiazolo[4,5-b]pyridin-6-yl)-2-(2-methylpyridin-4-yl)oxazole-4-carboxamide;

2-(2-acetamidopyridin-4-yl)-N-(5-(4-hydroxypiperidin-1-yl)-2-morpholinothiazolo[4,5-b]pyridin-6-yl)oxazole-4-carboxamide;

N-(2-(3-hydroxypiperidin-1-yl)-5-(4-hydroxypiperidin-1-yl)thiazolo[4,5-b]pyridin-6-yl)-2-(2-methylpyridin-4-yl)oxazole-4-carboxamide;

2-(2-acetamidopyridin-4-yl)-N-(5-(3-hydroxypiperidin-1-yl)-2-morpholinothiazolo[4,5-b]pyridin-6-yl)oxazole-4-carboxamide;

2-(2-aminopyridin-4-yl)-N-(5-(3-hydroxypiperidin-1-yl)-2-morpholinothiazolo[4,5-b]pyridin-6-yl)oxazole-4-carboxamide hydrochloride;

5-(2-aminopyridin-4-yl)-N-(5-(4-hydroxypiperidin-1-yl)-2-morpholinothiazolo[4,5-b]pyridin-6-yl)furan-3-carboxamide hydrochloride;

2-(2-aminopyridin-4-yl)-N-(5-(4-hydroxypiperidin-1-yl)-2-morpholinothiazolo[4,5-b]pyridin-6-yl)oxazole-4-carboxamide hydrochloride;

2-(2-aminopyridin-4-yl)-N-(5-(4-fluoropiperidin-1-yl)-2-morpholinothiazolo[4,5-b]pyridin-6-yl)oxazole-4-carboxamide hydrochloride;

N-(5-(2-fluoropyridin-4-yl)-2-morpholinothiazolo[4,5-b]pyridin-6-yl)-2-(2-methylpyridin-4-yl)oxazole-4-carboxamide;

N-(5-(4-fluoropiperidin-1-yl)-2-(3-hydroxypiperidin-1-yl)thiazolo[4,5-b]pyridin-6-yl)-2-(2-methylpyridin-4-yl)oxazole-4-carboxamide;

N-(5-(4-aminopiperidin-1-yl)-2-(3-hydroxypiperidin-1-yl)thiazolo[4,5-b]pyridin-6-yl)-2-(2-methylpyridin-4-yl)oxazole-4-carboxamide hydrochloride; and N-(5-(2-hydroxypyridin-4-yl)-2-morpholinothiazolo[4,5-b]pyridin-6-yl)-2-(2-methylpyridin-4-yl)oxazole-4-carboxamide hydrochloride;

or a pharmaceutically acceptable salt or a stereoisomer thereof.

In some embodiments, the compound of Formula (II) is Compound A.

In some embodiments, the BCL-2 inhibitor is venetoclax.

Provided herein is a method of treating or preventing cancer in a subject, comprising administering to the subject a compound of Formula (III) conjointly with a B-cell lymphoma 2 (BCL-2) inhibitor:

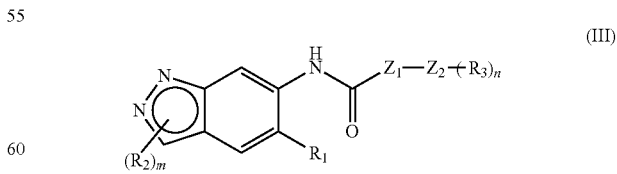

(III)

or a pharmaceutically acceptable salt thereof;
wherein,
$Z_1$ represents optionally substituted cycloalkyl, optionally substituted aryl, optionally substituted heterocyclyl or is absent;

$Z_2$ represents optionally substituted cycloalkyl, optionally substituted aryl or optionally substituted heterocyclyl;

$R_1$ is hydrogen, optionally substituted alkyl, amino, halo, cyano, optionally substituted cycloalkyl, optionally substituted aryl, optionally substituted heterocyclyl, optionally substituted arylalkyl or optionally substituted heterocyclylalkyl;

$R_2$ at each occurrence is amino, optionally substituted alkyl, optionally substituted cycloalkyl, optionally substituted aryl, optionally substituted heterocyclyl, optionally substituted arylalkyl or optionally substituted heterocyclylalkyl;

$R_3$ at each occurrence is hydroxy, halo, optionally substituted alkyl, optionally substituted alkoxy, optionally substituted cycloalkyl or —$NR_aR_b$;

$R_a$ and $R_b$, independently for each occurrence, are hydrogen, optionally substituted alkyl, optionally substituted acyl, optionally substituted cycloalkyl, optionally substituted aryl, optionally substituted heterocyclyl, optionally substituted arylalkyl or optionally substituted heterocyclylalkyl;

m, at each occurrence, is 0, 1 or 2; and n, at each occurrence, is 0, 1, or 2.

In some embodiments, the present methods include a compound of formula (III) or a pharmaceutically acceptable salt thereof, wherein $Z_1$ is an optionally substituted heterocyclyl.

In some embodiments, the present methods include a compound of formula (III) or a pharmaceutically acceptable salt thereof, wherein $Z_1$ represents cycloalkyl, aryl, or heterocyclyl, optionally substituted by one or more substituents selected, independently for each occurrence, from hydroxy, halo, alkyl, cycloalkyl, or $NR_aR_b$.

In some embodiments, the present methods include a compound of formula (III) or a pharmaceutically acceptable salt thereof, wherein $Z_1$ is an optionally substituted heteroaryl; wherein the optional substituent is alkyl or cycloalkyl.

In some embodiments, the present methods include a compound of formula (III) or a pharmaceutically acceptable salt thereof, wherein $Z_1$ is tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl, pyrazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and pyrazolopyrimidyl; each of which is optionally substituted.

In some embodiments, the present methods include a compound of formula (III) or a pharmaceutically acceptable salt thereof, wherein $Z_1$ is tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl or pyrazolyl.

In some embodiments, the present methods include a compound of formula (III) or a pharmaceutically acceptable salt thereof, wherein $Z_1$ is pyridyl or oxazolyl; wherein the oxazolyl group is optionally substituted with alkyl; in particular alkyl is methyl.

In some embodiments, the present methods include a compound of formula (III) or a pharmaceutically acceptable salt thereof, wherein $Z_1$ is absent.

In some embodiments, the present methods include a compound of formula (III) or a pharmaceutically acceptable salt thereof, wherein $Z_2$ is cycloalkyl, aryl or heterocyclyl.

In some embodiments, the present methods include a compound of formula (III) or a pharmaceutically acceptable salt thereof, wherein $Z_2$ represents cycloalkyl, aryl, or heterocyclyl, optionally substituted by one or more substituents selected from hydroxy, halo, alkyl, alkoxyl, cycloalkyl, —$NR_aR_b$, or cycloalkoxy.

In some embodiments, the present methods include a compound of formula (III) or a pharmaceutically acceptable salt thereof, wherein $Z_2$ is heterocyclyl.

In some embodiments, the present methods include a compound of formula (III) or a pharmaceutically acceptable salt thereof, wherein $Z_2$ is azetidinyl, oxetanyl, furanyl, piperidinyl, morpholinyl, piperazinyl, thiomorpholinyl, 1,4-dioxanyl, tetrahydropyranyl, tetrahydrofuranyl, tetrahydropyridyl, tetrazolyl, thienyl, triazolyl, pyrrolyl, pyridyl, pyranyl, pyrazinyl, pyridazinyl, pyrimidyl, imidazolidinyl, imidazolyl, thiadiazolyl, thiazolyl, thiazolidinyl, isothiazolyl, oxadiazolyl, oxazolyl, pyrazolyl, pyrrolidinyl, oxazolidinyl, pyrazolidinyl, benzisoxazolyl, benzothiazolyl, benzofuranyl, benzothienyl, benzotriazinyl, indolyl, isoindolyl, indazolyl, quinolinyl, isoquinolinyl pyrrolopyridyl or pyrazolopyrimidyl.

In some embodiments, the present methods include a compound of formula (III) or a pharmaceutically acceptable salt thereof, wherein $Z_2$ is pyridyl, piperazinyl, pyrimidyl, pyrrolidinyl, 1,2,3,4-tetrahydropyridyl, piperidinyl, pyrazolopyrimidyl or pyrrolopyridyl.

In certain embodiments, the compound of formula (III) is compound of formula (IIIA)

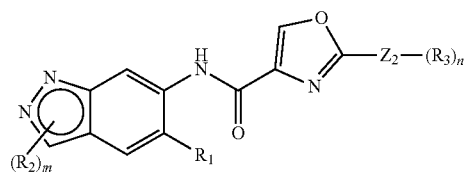

(IIIA)

or a pharmaceutically acceptable salt thereof;

wherein, $Z_2$, $R_1$, $R_2$, $R_3$, 'm', and 'n' are as defined in compound of formula (III).

In certain embodiments, the compound of formula (III) is compound of formula (IIIB)

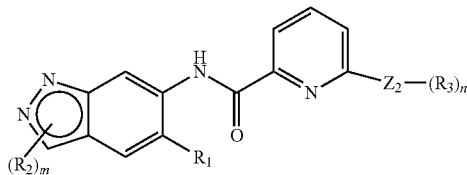

(IIIB)

or a pharmaceutically acceptable salt thereof;

wherein, $Z_2$, $R_1$, $R_2$, $R_3$, 'm', and 'n' are as defined in compound of formula (III).

In some embodiments, the present methods include a compound of formula (III) or a pharmaceutically acceptable salt thereof, wherein the group

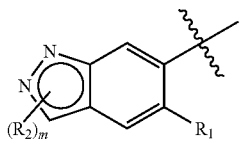

is

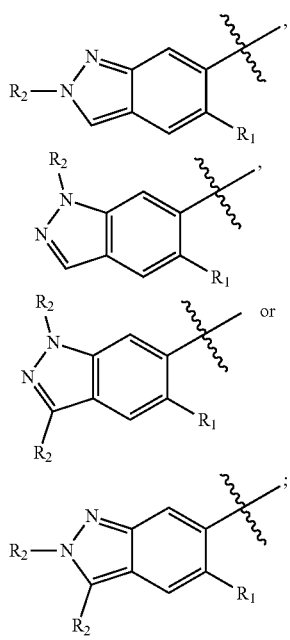

wherein $R_1$, $R_2$ and 'm' are same as defined in compound of formula (III).

In some embodiments, the present methods include a compound of formula (III) or a pharmaceutically acceptable salt thereof, wherein $Z_2$ is pyridyl.

In some embodiments, the present methods include a compound of formula (III) or a pharmaceutically acceptable salt thereof, wherein $Z_2$ is pyrrolidinyl.

In some embodiments, the present methods include a compound of formula (III) or a pharmaceutically acceptable salt thereof, wherein $Z_2$ is piperidinyl, piperazinyl, tetrahydropyridyl, pyrimidyl or pyrazolopyridyl.

In some embodiments, the present methods include a compound of formula (III) or a pharmaceutically acceptable salt thereof, wherein $R_1$ is hydrogen, optionally substituted alkyl, amino, halo, cyano, optionally substituted cycloalkyl, optionally substituted aryl, optionally substituted heterocyclyl, optionally substituted arylalkyl or optionally substituted heterocyclylalkyl.

In some embodiments, the present methods include a compound of formula (III) or a pharmaceutically acceptable salt, wherein $R_1$ is alkyl, cycloalkyl, aryl, heterocyclyl, arylalkyl, optionally substituted with one or more substituents selected, independently for each occurrence, from hydroxy, halo, alkyl, or hydroxyalkyl.

In some embodiments, the present methods include a compound of formula (III) or a pharmaceutically acceptable salt, wherein $R_1$ is heterocyclyl; optionally substituted with halogen, hydroxyl or hydroxyalkyl.

In some embodiments, the present methods include a compound of formula (III) or a pharmaceutically acceptable salt, wherein $R_1$ is optionally substituted azetidinyl, piperidinyl, morpholinyl, pyrrolidinyl or azepanyl.

In some embodiments, the present methods include a compound of formula (III) or a pharmaceutically acceptable salt, wherein $R_1$ is piperidinyl, optionally substituted with hydroxyl.

In some embodiments, the present methods include a compound of formula (III) or a pharmaceutically acceptable salt, wherein $R_1$ is pyrrolidinyl, optionally substituted with hydroxyl.

In some embodiments, the present methods include a compound of formula (III) or a pharmaceutically acceptable salt, wherein $R_2$, at each occurrence, is amino, optionally substituted alkyl, optionally substituted cycloalkyl, optionally substituted aryl, optionally substituted heterocyclyl, optionally substituted arylalkyl or optionally substituted heterocyclylalkyl.

In some embodiments, the present methods include a compound of formula (III) or a pharmaceutically acceptable salt, wherein $R_2$ is alkyl, cycloalkyl, aryl, heterocyclyl, arylalkyl, or heterocyclylalkyl, optionally substituted with one or more substituents selected, independently for each occurrence, from alkyl, cycloalkyl, or heterocyclyl.

In some embodiments, the present methods include a compound of formula (III) or a pharmaceutically acceptable salt thereof, wherein $R_2$ is optionally substituted alkyl, preferably, methyl.

In some embodiments, the present methods include a compound of formula (III) or a pharmaceutically acceptable salt thereof, wherein $R_2$ is optionally substituted cycloalkyl, preferably, cyclopropyl.

In some embodiments, the present methods include a compound of formula (III) or a pharmaceutically acceptable salt thereof, wherein $R_3$, at each occurrence, is hydroxy, halo, optionally substituted alkyl, optionally substituted alkoxy, optionally substituted cycloalkyl or —$NR_aR_b$; wherein $R_a$ is hydrogen or optionally substituted alkyl; and $R_b$ is hydrogen, optionally substituted alkyl, optionally substituted acyl, hydroxyalkyl or —$SO_2$-alkyl.

In some embodiments, the present methods include a compound of formula (III) or a pharmaceutically acceptable salt thereof, wherein $Z_1$ is optionally substituted pyridyl; $Z_2$ is pyrrolidinyl; $R_1$ is an optionally substituted groups selected from piperidinyl or pyrrolidinyl; $R_2$ is optionally substituted alkyl; $R_3$ is halogen, alkyl, —$NR_aR_b$, hydroxyl or hydroxyalkyl; $R_a$ is hydrogen or alkyl; and $R_b$ is hydrogen or hydroxyalkyl.

In some embodiments, the present methods include a compound of formula (III) or a pharmaceutically acceptable salt thereof, wherein $Z_1$ is oxazolyl; $Z_2$ is pyridyl, pyrimidyl or pyrrolidinyl, piperidinyl, tetrahydropyridyl, piperazinyl, pyrrolopyridyl; $R_1$ is an optionally substituted group selected from piperidinyl or pyrrolidinyl; $R_2$ is optionally substituted alkyl or cyclopropyl; $R_3$ is halogen, alkyl, alkoxy, —$NR_aR_b$, hydroxyl, hydroxyalkyl optionally substituted cyclopropyl; $R_a$ is hydrogen or alkyl; and $R_b$ is hydrogen, alkyl, acyl, hydroxyalkyl, —$SO_2$-alkyl or optionally substituted cycloalkyl.

In some embodiments, the present methods include a compound of formula (III) or a pharmaceutically acceptable salt thereof, wherein 'm' is 0.

In some embodiments, the present methods include a compound of formula (III) or a pharmaceutically acceptable salt thereof, wherein 'm' is 1.

In some embodiments, the present methods include a compound of formula (III) or a pharmaceutically acceptable salt thereof, wherein 'm' is 2.

In some embodiments, the present methods include a compound of formula (III) or a pharmaceutically acceptable salt thereof, wherein 'n' is 0.

In some embodiments, the present methods include a compound of formula (III) or a pharmaceutically acceptable salt thereof, wherein 'n' is 1.

In some embodiments, the present methods include a compound of formula (III) or a pharmaceutically acceptable salt thereof, wherein 'n' is 2.

In some embodiments, the present methods include a compound of formula (III) selected from:

N-(1-methyl-5-(piperidin-1-yl)-1H-indazol-6-yl)-2-(2-methylpyridin-4-yl)oxazole-4-carboxamide hydrochloride;

N-(2-methyl-5-(piperidin-1-yl)-2H-indazol-6-yl)-2-(2-methylpyridin-4-yl)oxazole-4-carboxamide hydrochloride;

(S)-6-(3-hydroxypyrrolidin-1-yl)-N-(2-methyl-5-(piperidin-1-yl)-2H-indazol-6-yl)picolinamide;

(S)-2-(3-aminopyrrolidin-1-yl)-N-(1-methyl-5-(piperidin-1-yl)-1H-indazol-6-yl)oxazole-4-carboxamide;

(S)-2-(3-aminopyrrolidin-1-yl)-N-(2-methyl-5-(piperidin-1-yl)-2H-indazol-6-yl)oxazole-4-carboxamide;

(S)-2-(3-hydroxypyrrolidin-1-yl)-N-(2-methyl-5-(piperidin-1-yl)-2H-indazol-6-yl)oxazole-4-carboxamide;

(S)-6-(3-aminopyrrolidin-1-yl)-N-(2-methyl-5-(piperidin-1-yl)-2H-indazol-6-yl)picolinamide (S)-6-(3-aminopyrrolidin-1-yl)-N-(1-methyl-5-(piperidin-1-yl)-1H-indazol-6-yl)picolinamide;

(S)-6-(3-hydroxypyrrolidin-1-yl)-N-(1-methyl-5-(piperidin-1-yl)-1H-indazol-6-yl)picolinamide;

(S)-2-(3-hydroxypyrrolidin-1-yl)-N-(1-methyl-5-(piperidin-1-yl)-1H-indazol-6-yl)oxazole-4-carboxamide;

(S)—N-(5-(3-hydroxypyrrolidin-1-yl)-1-methyl-1H-indazol-6-yl)-2-(2-methylpyridin-4-yl)oxazole-4-carboxamide;

N-(5-(3-hydroxypiperidin-1-yl)-1-methyl-1H-indazol-6-yl)-2-(2-methylpyridin-4-yl)oxazole-4-carboxamide N-(5-(3-hydroxypiperidin-1-yl)-2-methyl-2H-indazol-6-yl)-2-(2-methylpyridin-4-yl)oxazole-4-carboxamide N-(5-(3-fluoropiperidin-1-yl)-2-methyl-2H-indazol-6-yl)-2-(2-methylpyridin-4-yl)oxazole-4-carboxamide;

(S)-2-(2-acetamidopyridin-4-yl)-N-(5-(3-hydroxypyrrolidin-1-yl)-1-methyl-1H-indazol-6-yl)oxazole-4-carboxamide;

N-(5-(3-fluoropiperidin-1-yl)-1-methyl-1H-indazol-6-yl)-2-(2-methylpyridin-4-yl)oxazole-4-carboxamide;

N-(5-(4-hydroxypiperidin-1-yl)-1-methyl-1H-indazol-6-yl)-2-(2-methylpyridin-4-yl)oxazole-4-carboxamide;

(S)-2-(2-aminopyridin-4-yl)-N-(5-(3-hydroxypyrrolidin-1-yl)-1-methyl-1H-indazol-6-yl)oxazole-4-carboxamide;

N-(5-(4-fluoropiperidin-1-yl)-1-methyl-1H-indazol-6-yl)-2-(2-methylpyridin-4-yl)oxazole-4-carboxamide;

N-(5-(4-(hydroxymethyl)piperidin-1-yl)-1-methyl-1H-indazol-6-yl)-2-(2-methylpyridin-4-yl)oxazole-4-carboxamide;

(S)-2-(2,6-dimethylpyridin-4-yl)-N-(5-(3-hydroxypyrrolidin-1-yl)-1-methyl-1H-indazol-6-yl)oxazole-4-carboxamide;

(R)—N-(5-(3-hydroxypyrrolidin-1-yl)-1-methyl-1H-indazol-6-yl)-2-(2-methylpyridin-4-yl)oxazole-4-carboxamide;

(S)-2-(2-aminopyridin-3-yl)-N-(5-(3-hydroxypyrrolidin-1-yl)-1-methyl-1H-indazol-6-yl)oxazole-4-carboxamide Hydrochloride;

6-((S)-3-hydroxypyrrolidin-1-yl)-N-(5-((R)-3-hydroxypyrrolidin-1-yl)-1-methyl-1H-indazol-6-yl)picolinamide;

(S)—N-(5-(3-hydroxypyrrolidin-1-yl)-1-methyl-1H-indazol-6-yl)pyrazolo[1,5-a]pyrimidine-3-carboxamide;

6-((S)-3-hydroxypyrrolidin-1-yl)-N-(5-((S)-3-hydroxypyrrolidin-1-yl)-1-methyl-1H-indazol-6-yl) picolinamide;

(S)—N-(5-(3-hydroxypyrrolidin-1-yl)-1-methyl-1H-indazol-6-yl)-2-(1H-pyrrolo[2,3-b]pyridin-4-yl)oxazole-4-carboxamide;

(S)—N-(5-(3-hydroxypyrrolidin-1-yl)-1H-indazol-6-yl)-2-(2-methylpyridin-4-yl)oxazole-4-carboxamide;

(S)-2-(2-amino-3-fluoropyridin-4-yl)-N-(5-(3-hydroxypyrrolidin-1-yl)-1-methyl-1H-indazol-6-yl)oxazole-4-carboxamide;

(R)-2-(2-aminopyridin-3-yl)-N-(5-(3-hydroxypyrrolidin-1-yl)-1-methyl-1H-indazol-6-yl)oxazole-4-carboxamide hydrochloride;

(S)—N-(5-(3-hydroxypyrrolidin-1-yl)-1-methyl-1H-indazol-6-yl)-2-(4-methylpiperazin-1-yl)oxazole-4-carboxamide;

(S)—N-(5-(3-hydroxypyrrolidin-1-yl)-1-methyl-1H-indazol-6-yl)-2-(piperazin-1-yl)oxazole-4-carboxamide;

(S)—N-(1-ethyl-5-(3-hydroxypyrrolidin-1-yl)-1H-indazol-6-yl)-2-(2-methylpyridin-4-yl)oxazole-4-carboxamide hydrochloride;

(S)—N-(1-cyclopropyl-5-(3-hydroxypyrrolidin-1-yl)-1H-indazol-6-yl)-2-(2-methylpyridin-4-yl)oxazole-4-carboxamide hydrochloride;

(S)—N-(5-(3-hydroxypyrrolidin-1-yl)-1-methyl-1H-indazol-6-yl)-2-(1,2,3,6-tetrahydropyridin-4-yl)oxazole-4-carboxamide hydrochloride;

(S)—N-(5-(3-hydroxypyrrolidin-1-yl)-1-methyl-1H-indazol-6-yl)-2-(2-methylpyrimidin-4-yl)oxazole-4-carboxamide;

(S)—N-(5-(3-hydroxypyrrolidin-1-yl)-1-methyl-1H-indazol-6-yl)-4-methyl-2-(2-methylpyridin-4-yl) oxazole-5-carboxamide;

(S)—N-(5-(3-hydroxypyrrolidin-1-yl)-1-methyl-1H-indazol-6-yl)-2-(piperidin-4-yl)oxazole-4-carboxamide hydrochloride;

N-(5-(3-hydroxy-8-azabicyclo[3.2.1]octan-8-yl)-1-methyl-1H-indazol-6-yl)-2-(2-methylpyridin-4-yl)oxazole-4-carboxamide;

(S)—N-(5-(3-hydroxypyrrolidin-1-yl)-1-methyl-1H-indazol-6-yl)-2-(2-methylpyridin-4-yl) oxazole-5-carboxamide;

N-(5-(4-hydroxy-4-(hydroxymethyl)piperidin-1-yl)-1-methyl-1H-indazol-6-yl)-2-(2-methylpyridin-4-yl)oxazole-4-carboxamide hydrochloride;

(S)—N-(5-(3-hydroxypyrrolidin-1-yl)-1-methyl-1H-indazol-6-yl)-5-methyl-2-(2-methylpyridin-4-yl)oxazole-4-carboxamide;

(S)-2-(2-ethylpyridin-4-yl)-N-(5-(3-hydroxypyrrolidin-1-yl)-1-methyl-1H-indazol-6-yl)oxazole-4-carboxamide;

2-(2-aminopyridin-4-yl)-N-(5-(4-(hydroxymethyl)piperidin-1-yl)-1,3-dimethyl-1H-indazol-6-yl)oxazole-4-carboxamide hydrochloride;

(S)—N-(5-(3-hydroxypyrrolidin-1-yl)-1-(piperidin-4-ylmethyl)-1H-indazol-6-yl)-2-(2-methylpyridin-4-yl)oxazole-4-carboxamide;

N-(5-(4-(hydroxymethyl)piperidin-1-yl)-1,3-dimethyl-1H-indazol-6-yl)-2-(2-methylpyridin-4-yl)oxazole-4-carboxamide;

(S)-2-(2-cyclopropylpyridin-4-yl)-N-(5-(3-hydroxypyrrolidin-1-yl)-1-methyl-1H-indazol-6-yl)oxazole-4-carboxamide; and N-(5-(4-hydroxypiperidin-1-yl)-2-methyl-2H-indazol-6-yl)pyrazolo[1,5-a]pyrimidine-3-carboxamide;

In some embodiments, the compound of Formula (III) is Compound A.

In some embodiments, the BCL-2 inhibitor is venetoclax.

Pharmaceutical Compositions

In certain embodiments, the present methods include a pharmaceutical composition comprising the compound as disclosed herein, optionally admixed with a pharmaceutically acceptable carrier or diluent.

As used herein, the term "composition" is intended to encompass a product comprising the specified ingredients in the specified amounts, as well as any product which results, directly or indirectly, from combination of the specified ingredients in the specified amounts.

As used herein, the term "pharmaceutical composition" refers to a composition(s) containing a therapeutically effective amount of at least one compound of formula (I) or its pharmaceutically acceptable salt; and a conventional pharmaceutically acceptable carrier.

The pharmaceutical composition(s) of the present invention can be administered orally, for example in the form of tablets, coated tablets, pills, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of ointments or creams or transdermals, in the form of patches, or in other ways, for example in the form of aerosols or nasal sprays.

The pharmaceutical composition(s) usually contain(s) about 1% to 99%, for example, about 5% to 75%, or from about 10% to about 30% by weight of the compound of formula (I) or pharmaceutically acceptable salts thereof. The amount of the compound of formula (I) or pharmaceutically acceptable salts thereof in the pharmaceutical composition(s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

The present invention also provides methods for formulating the disclosed compounds as for pharmaceutical administration.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, about 0.1 to about 99.5% (more preferably, about 0.5 to about 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required.

For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The compounds of the present invention may be administered in combination with one or more other drugs (1) to complement and/or enhance prevention and/or therapeutic efficacy of the preventive and/or therapeutic drug effect of the compound of the present invention, (2) to modulate pharmacodynamics, improve absorption improvement, or reduce dosage reduction of the preventive and/or therapeutic compound of the present invention, and/or (3) to reduce or ameliorate the side effects of the preventive and/or therapeutic compound of the present invention. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds. The respective compounds may be administered by the same or different route and the same or different method.

A concomitant medicine comprising the compounds of the present invention and other drug may be administered as a combination preparation in which both components are contained in a single formulation, or administered as separate formulations. The administration by separate formulations includes simultaneous administration and or administration of the formulations separated by some time intervals. In the case of the administration with some time intervals, the compound of the present invention can be administered first, followed by another drug or another drug can be administered first, followed by the compound of the present invention, so long as the two compounds are simultaneously active in the patient at least some of the time during the conjoint therapy. The administration method of the respective drugs may be administered by the same or different route and the same or different method.

The dosage of the other drug can be properly selected, based on a dosage that has been clinically used, or may be a reduced dosage that is effective when administered in combination with a compound of the present invention. The compounding ratio of the compound of the present invention and the other drug can be properly selected according to age and weight of a subject to be administered, administration method, administration time, disorder to be treated, symptom and combination thereof. For example, the other drug may be used in an amount of about 0.01 to about 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

In certain embodiments, a compound of the invention may be conjointly administered with non-chemical methods of cancer treatment. In certain embodiments, a compound of the invention may be conjointly administered with radiation therapy. In certain embodiments, a compound of the invention may be conjointly administered with surgery, with thermoablation, with focused ultrasound therapy, with cryotherapy, or with any combination of these.

Methods of Treatment

DLBCL is an aggressive lymphoma that can arise in lymph nodes or outside of the lymphatic system, in the gastrointestinal tract, testes, thyroid, skin, breast, bone, or brain. DLBCL is a cancer of B cells, a type of white blood cell responsible for producing antibodies. Usually DLBCL arises from normal B cells, but it can also represent a malignant transformation of other types of lymphoma or leukemia. DLBCL has subtypes that are named according to their cell of origin and include germinal center B-cell-like (GCB) and activated B-cell-like (ABC), each having a different clinical presentation and prognosis. Tumor cells in the germinal center B-cell-like subgroup resemble normal B cells in the germinal center closely, and are generally associated with a favorable prognosis. Activated B-cell-like tumor cells are associated with a poorer prognosis, and derive their name from studies which show the continuous activation of certain pathways normally activated when B cells interact with an antigen. The NF-κB pathway, which is normally involved in transforming B cells into plasma cells, is an important example of one such pathway.

IRAK-4 kinase activity is required for toll-like receptor (TLR) and interleukin-1 receptor (IL-1R) signaling in a variety of myeloid and lymphoid cell types. Recruitment of IRAK4 to these receptors and its subsequent activation is facilitated by the MYD88 adaptor protein, which is mutated in ~22% of DLBCL cases. The MYD88 L265P activating mutation is found in ~30% of the ABC and ~6% of GCB subtypes of DLBCL and leads to constitutive activation of NF-kB signaling that is associated with worse prognosis. In Waldenstrom's macroglobulinemia (WM), the MYD88-L265P activating mutation is present in >90% of cases.

Certain IRAK-4 inhibitors, such as Compound A disclosed herein, exhibit dose-dependent efficacy in ABC-DLBCL MYD88-L265P xenograft tumor models using cell lines OCI-LY3 and OCI-LY10. Compound A is efficacious in ABC-DLBCL PDX tumors containing activating mutations in both TLR/IL-1R and B-cell receptor (BCR) signaling pathways (MYD88 and CD79B double mutants). The BCR pathway is indirectly affected by non-kinase targets, such as B-cell lymphoma 2 (BCL-2) inhibitors. Treatment with an IRAK-4 inhibitor alone and treatment with a BCL-2 inhibitor, such as venetoclax, alone did not result in significant tumor response. However, treatment with both an IRAK-4 inhibitor and a BCL-2 inhibitor has demonstrated a synergistic tumor growth inhibition effect.

Disclosed herein are methods for treating or preventing diffuse large B-cell lymphoma or Waldenstrom's macroglobulinemia that comprise administering a disclosed compound with a BCL-2 inhibitor. In some embodiments, the DLBCL is activated B-cell like DLBCL. In some embodiments, the DLBCL is characterized by a L265P mutation in MYD88 and/or a BCL translocation. In some embodiments, the BCL-2 inhibitor is venetoclax (ABT-199).

Non-Hodgkin's Lymphomas

The combination of an IRAK-4 inhibitor and a BCL-2 inhibitor can be advantageous in treating or preventing other non-Hodgkin's lymphomas, such as mantle cell lymphoma (MCL), marginal zone lymphoma (MZL), follicular lymphoma (FL), chronic lymphocytic leukemia (CLL), small lymphocytic lymphoma (SLL), CNS lymphoma, and testicular lymphoma. Non-Hodgkin's lymphomas are cancers that begin in white blood cells called lymphocytes. These cancers can affect B-cells or T-cells, with B-cell lymphomas being more prevalent. Indolent lymphomas grow slowly, such as FL and MZL. Aggressive lymphomas that rapidly grow include DLBCL.

MZL often occurs in the stomach. Mucosa-associated lymphoid tissue (MALT) lymphoma is the most common form of marginal zone lymphoma that occurs outside the lymph nodes. Other types include nodal marginal zone lymphoma occurring inside the lymph nodes and splenic marginal zone lymphoma within the spleen.

FL is a lymphoma of follicle center B-cells (centrocytes and centroblasts), which has at least a partially follicular pattern. It is caused by a translocation between chromosome 14 and 18 that results in the overexpression of the bcl-2 gene. The tumor is composed of follicles containing a mixture of centrocytes (cleaved follicle center cells) and centroblasts (large noncleaved follicle center cells). These follicles are surrounded by non-malignant cells, mostly T-cells. In the follicles, centrocytes typically predominate; centroblasts are usually in the minority.

CLL is the most common type of leukemia. CLL affects B cell lymphocytes, which originate in the bone marrow, develop in the lymph nodes, and normally fight infection by producing antibodies. In CLL, B cells grow in an uncontrolled manner and accumulate in the bone marrow and blood, where they crowd out healthy blood cells. CLL is a stage of small lymphocytic lymphoma (SLL), a type of B-cell lymphoma, which presents primarily in the lymph nodes. CLL and SLL are considered the same underlying disease, just with different appearances. Most people are diagnosed without symptoms as the result of a routine blood test that shows a high white blood cell count. As it advances, CLL results in swollen lymph nodes, spleen, and liver, and eventually anemia and infections.

CNS lymphoma, also known as microglioma and primary brain lymphoma, is a primary intracranial tumor appearing mostly in patients with severe immunodeficiency (typically patients with AIDS). CNS lymphoma is highly associated with Epstein-Barr virus (EBV) infection (>90%) in immunodeficient patients (such as those with AIDS and those immunosuppressed). CNS lymphoma is a type of DLBCL.

Testicular lymphoma is a rare extranodal presentation of non-Hodgkin's lymphoma.

Testicular lymphoma is a type of DLBCL. Testicular lymphoma is frequently associated with Burkitt's NHL and non-Burkitt's small-cell NHL, T-ALL, primary testicular diffuse large-cell lymphoma, HIV-associated aggressive B-cell lymphoma, and HTLV-1 associated lymphoma.

Lymphoma is the most common secondary testicular cancer. Among men older than 50, testicular lymphoma is more common than primary testicular tumors.

Leukemias

The combination of an IRAK-4 inhibitor and a BCL-2 inhibitor can be advantageous in treating or preventing leukemia including, but not limited to, acute myeloid leukemia (AML) and myelodysplastic syndromes (MDS). Leukemia is a group of cancers that usually begin in the bone marrow and result in high numbers of abnormal white blood cells. These white blood cells are not fully developed and are called blasts or leukemia cells. The exact cause of leukemia is unknown.

In acute lymphoblastic leukemia (ALL) and AML, a rapid increase in the number of immature blood cells occurs. The crowding that results from such cells makes the bone marrow unable to produce healthy blood cells. Immediate treatment is required in acute leukemia because of the rapid progression and accumulation of the malignant cells, which then spill over into the bloodstream and spread to other organs of the body. In chronic lymphocytic leukemia (CLL) and chronic myelogenous leukemia (CML), an excessive buildup of relatively mature, but still abnormal, white blood cells occurs. Typically taking months or years to progress, the cells are produced at a much higher rate than normal, resulting in many abnormal white blood cells. Whereas acute leukemia is treated immediately, chronic forms are sometimes monitored for some time before treatment to ensure maximum effectiveness of therapy. In ALL and CLL, the cancerous change takes place in a type of marrow cell that normally goes on to form lymphocytes, which are infection-fighting immune system cells. Most lymphocytic leukemias involve a specific subtype of lymphocyte, the B cell. In AML and CML, the cancerous change takes place in a type of marrow cell that normally goes on to form red blood cells, some other types of white cells, and platelets.

Myelodysplastic syndromes are a group of cancers in which immature blood cells in the bone marrow do not mature and therefore do not become healthy blood cells. Some types may develop into acute myeloid leukemia. The World Health Organization has identified the following categories of myelodysplastic syndrome: refractory anemia, refractory anemia with ringed sideroblasts, refractory anemia with excess blasts in transformation, and chronic myelomonocytic leukemia. Risk factors for developing one of these syndromes include previous chemotherapy or radiation therapy, exposure to certain chemicals such as tobacco smoke, pesticides, and benzene, and exposure to heavy metals such as mercury or lead. Problems with blood cell formation result in some combination of low red blood cells, low platelets, and low white blood cells. Some types have an increase in immature blood cells, called blasts, in the bone marrow or blood. The types of MDS are based on specific changes in the blood cells and bone marrow. The typical survival rate following diagnosis is 2.5 years.

Myeloproliferative Neoplasms

Myeloproliferative neoplasms include chronic myelogenous leukemia (CML), chronic neutrophilic leukemia (CNL), polycythemia vera (PCV), primary myelofibrosis, essential thrombocythemia, chronic eosinophilic leukemia, and mastocytosis. CNL is a rare myeloproliferative neoplasm that features a persistent neutrophilia in peripheral blood, myeloid hyperplasia in bone marrow, and concomitant enlargement of liver and spleen. CNL can affect blood, bone marrow, spleen, and liver, or other tissue that can be infiltrated with neutrophils.

Polycythemia vera (PCV) is an uncommon neoplasm in which the bone marrow makes too many red blood cells. It may also result in the overproduction of white blood cells and platelets. Being a primary polycythemia, polycythemia vera is caused by neoplastic proliferation and maturation of erythroid, megakaryocytic and granulocytic elements to produce what is referred to as panmyelosis. In contrast to secondary polycythemias, PCV is associated with a low serum level of the hormone erythropoietin (EPO).

Primary myelofibrosis is a relatively rare bone marrow cancer in which the proliferation of an abnormal clone of hematopoietic stem cells in the bone marrow and other sites results in fibrosis, or the replacement of the marrow with scar tissue. Myelofibrosis can develop secondary to polycythemia vera or essential thrombocythaemia. Myelofibrosis is a form of myeloid metaplasia, which refers to a change in cell type in the blood-forming tissue of the bone marrow. Production of cytokines such as fibroblast growth factor by the abnormal hematopoietic cell clone (particularly by megakaryocytes) leads to replacement of the hematopoietic tissue of the bone marrow by connective tissue via collagen fibrosis. The decrease in hematopoietic tissue impairs the patient's ability to generate new blood cells, resulting in progressive pancytopenia, a shortage of all blood cell types. Progressive scarring, or fibrosis, of the bone marrow occurs and haemopoetic cells are forced to migrate to other areas, particularly the liver and spleen, which become enlarged.

Essential thrombocythemia is a rare chronic blood condition characterized by the overproduction of platelets by megakaryocytes in the bone marrow. It may, albeit rarely, develop into acute myeloid leukemia or myelofibrosis. Megakaryocytes are more sensitive to growth factors. Platelets derived from the abnormal megakaryocytes are activated, which, along with the elevated platelet count, contributes to the likelihood of thrombosis.

Chronic eosinophilic leukemia is characterized by an excess of eosinophils (a type of white blood cell) that are found in the bone marrow, blood, and other tissues. Chronic eosinophilic leukemia may stay the same for many years, or it may progress quickly to acute leukemia.

Mastocytosis is a rare mast cell activation disorder of both children and adults caused by the presence of too many mast cells (mastocytes) and CD34+ mast cell precursors. Mast cells are located in connective tissue, including the skin, the linings of the stomach and intestine, and other sites. They play an important role in helping defend these tissues from disease. By releasing chemical "alarms" such as histamine, mast cells attract other key players of the immune defense system to areas of the body where they are needed. People affected by mastocytosis are susceptible to itching, hives, and anaphylactic shock, caused by the release of histamine from mast cells. The most common cutaneous mastocytosis is urticaria pigmentosa, often seen in children.

Solid Malignant Tumors

Sarcomas, carcinomas, melanomas, and glioblastomas are the main types of solid malignant tumor. Sarcomas are tumors in a blood vessel, bone, fat tissue, ligament, lymph vessel, muscle or tendon. Carcinomas are tumors that form in epithelial cells. Epithelial cells are found in the skin, glands and the linings of organs. Melanomas are tumors that develop in the pigment-containing cells known as melanocytes. Glioblastoma is an aggressive cancer that begins in the brain. They can either start from normal brain cells or develop from an existing low-grade astrocytoma. A solid tumor grows in an anatomical site outside the bloodstream (in contrast, for example, to cancers of hematopoietic origin such as leukemias) and requires the formation of small blood vessels and capillaries to supply nutrients, etc. to the growing tumor mass.

Non-limiting examples of solid malignant tumors include biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma, glioblastomas; medulloblastoma), cervical cancer (e.g., cervical adenocarcinoma), colorectal cancer (e.g., colon cancer, rectal cancer, colorectal adenocarcinoma), gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), pancreatic cancer (e.g., pancreatic andenocarcinoma, intraductal papillary mucinous neoplasm (IPMN)), prostate cancer (e.g., prostate adenocarcinoma), skin cancer (e.g., squamous cell carcinoma (SCC), keratoacanthoma (A), melanoma, basal cell carcinoma (BCC)) and soft tissue sarcoma (e.g., malignant fibrous histiocytoma (MFH), liposarcoma, malignant peripheral nerve sheath tumor (MPNST), chondrosarcoma, fibrosarcoma, myxosarcoma, osteosarcoma).

Additional Malignancies

In addition to the cancers discussed above, the disclosed methods are useful in the treatment of a wide variety of cancers.

In certain embodiments, the cancer is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, fibrosarcoma, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenstrim Macroglobulinemia, or Wilms Tumor.

In further embodiments of the invention, the cancer is selected from bladder cancer, breast cancer, esophageal cancer, gastric cancer, head & neck cancer, Kaposi's sarcoma, lung cancer (including non-small cell lung cancer and small cell lung cancer), melanoma, ovarian cancer, pancreatic cancer, penile cancer, prostate cancer, testicular germ-cell cancer, thymoma and thymic carcinoma.

Disclosed herein are methods for treating or preventing other B-cell non-Hodgkin lymphoma (NHL) subtypes including, but not limited to, mantle cell lymphoma (MCL), marginal zone lymphoma (MZL), follicular lymphoma (FL), chronic lymphocytic leukemia (CLL), small lymphocytic lymphoma (SLL), CNS lymphoma, and testicular lymphoma that comprise administering a disclosed compound with a BCL-2 inhibitor.

Disclosed herein are methods for treating or preventing leukemia including, but not limited to, acute myeloid leukemia (AML) and myelodysplastic syndromes (MDS) that comprise administering a disclosed compound with a BCL-2 inhibitor. Also disclosed herein are methods for treating or preventing myeloproliferative neoplasms and solid tumor cancers, including, but not limited to, pancreatic cancer and breast cancer.

In some embodiments, conjointly administering the BCL-2 inhibitor provides improved efficacy relative to separately administering the compound of formula (I), the compound of formula (II), or the compound of formula (III), and the BCL-2 inhibitor. In certain embodiments, conjointly administering the BCL-2 inhibitor provides a synergistic effect.

In some embodiments, the compound of formula (I), the compound of formula (II), or the compound of formula (III), and the BCL-2 inhibitor are administered simultaneously. In other embodiments, the BCL-2 inhibitor is administered within about 5 minutes to within about 168 hours prior to or after administration of the compound of formula (I), the compound of formula (II), or the compound of formula (III).

In certain embodiments, the present invention relates to a compound, or a pharmaceutically acceptable salt thereof as disclosed herein, for use in treating or preventing DLBCL or WM conjointly with a BCL-2 inhibitor as discussed herein. In certain embodiments, the present invention relates to use of a compound or a pharmaceutically acceptable salt thereof as disclosed herein, for the preparation of a medicament for treating or preventing DLBCL or WM conjointly with a BCL-2 inhibitor as discussed herein.

Compounds suitable for the compositions and methods disclosed herein can be found in are disclosed in WO2015/104662, WO2015/104688, and WO2015/193846, each of which is incorporated by reference in its entirety, and in particular for the compounds disclosed therein as IRAK-4 inhibitors.

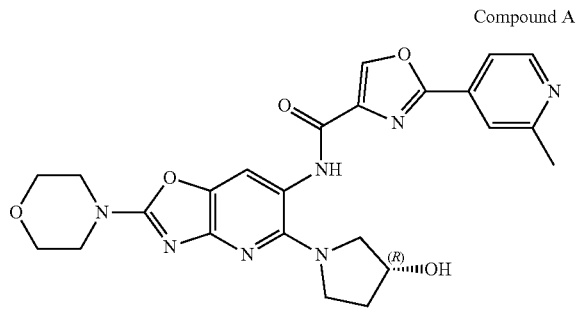

Compound A

Example 1: In Vivo Tumor Growth Inhibition in ABC-DLBCL Tumor Model

Figure 2:
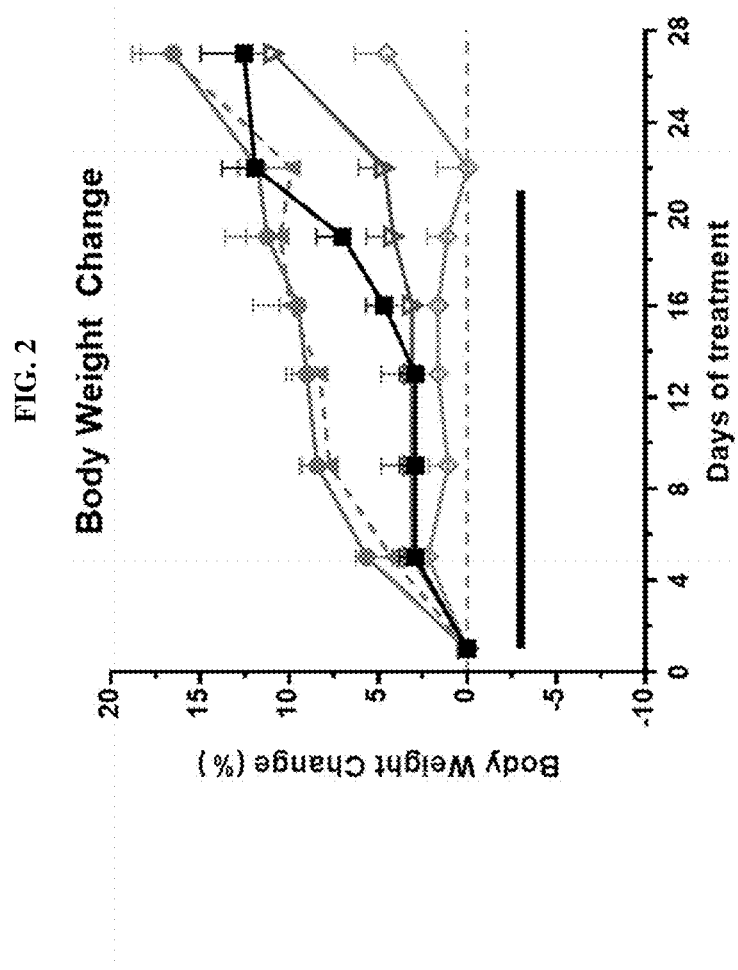
FIG. 2 shows the body weight change in the three groups of tumor-bearing mice that had been treated with Compound A, venetoclax or a combination thereof depicted in FIG. 1.

Female SCID Beige mice were implanted with the ABC-DLBCL cell line OCI-Ly10, which harbors TLR (MYD88-L265P) and BCR (CD79A ITAM) pathway activating mutations. The mice were treated with Compound A (50 mg/kg, qd, po, suspension in 0.5% Tween 20 and 0.25% hydroxyethyl cellulose), venetoclax (75 mg/kg, qd, po, solution in 60% phosal 50PG, 30% PEG 400, and 10% ethanol) or the combination for 21 continuous days. Single agent treatment with Compound A and venetoclax exhibited moderate tumor growth inhibition (TGI) of 63% and 71%, respectively, and the combination demonstrated tumor regression (REG). FIG. 1 illustrates these effects on tumor growth. The combination was tolerated at the end of treatment without body weight loss relative to predose weight as shown in FIG. 2.

Figure 3:
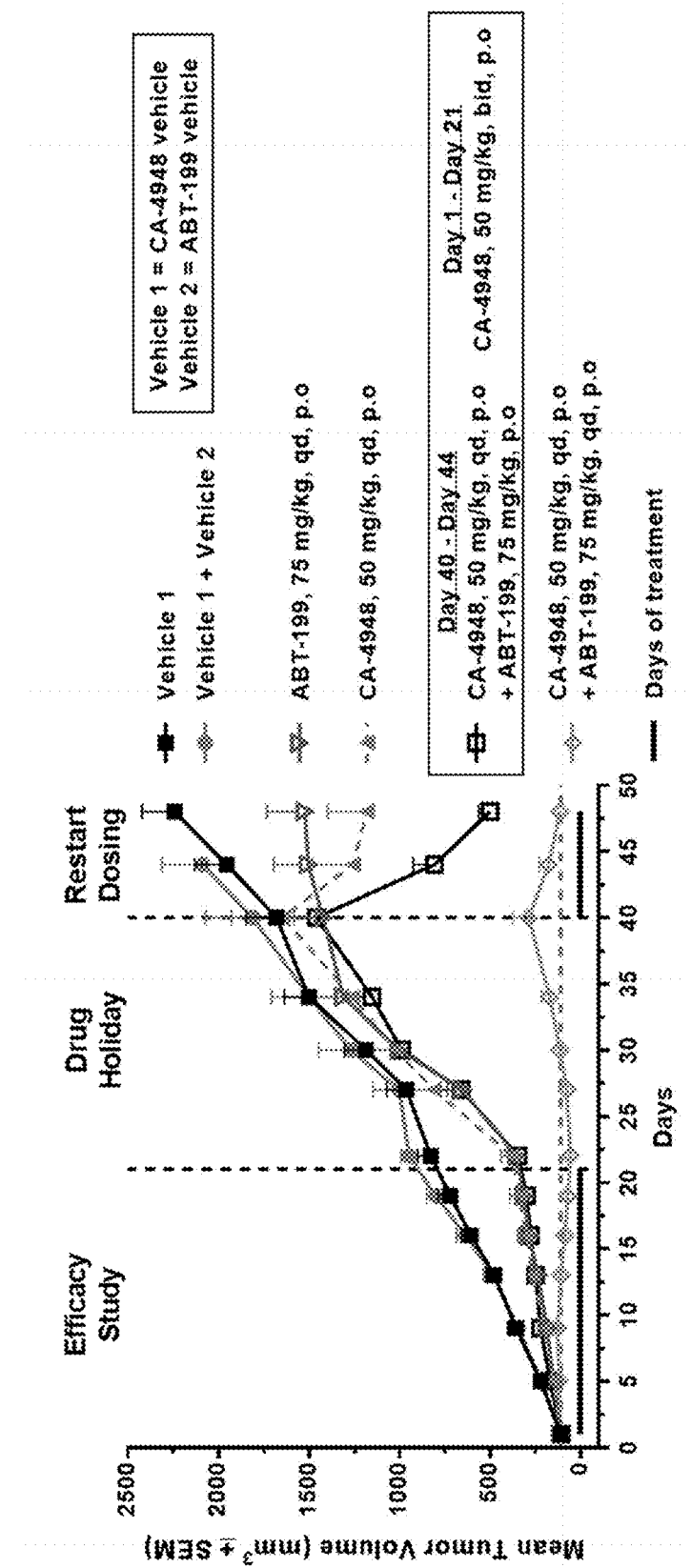
FIG. 3 shows the tumor growth response in the three groups of mice depicted in FIG. 1 after a 19 day drug holiday followed by resuming prior treatment.

After the 21-day drug treatment period, the mice were given a 19-day dosing holiday. Within 5 days of the holiday, rapid tumor growth occurred in the previously treated single drug-treated mice and this rapid growth continued for the remainder of the dosing holiday as shown in FIG. 3. In contrast, tumors from the combination drug-treated mice did not commence detectable regrowth until the 10th day of the drug holiday and proceeded with a slow growth rate for the subsequent 9 days. After the 19-day drug holiday, dosing of the respective drug treatments was reinstated to each cohort. After 7 days of re-dosing, the tumors in each cohort exhibited antitumor responses to respective drug treatments with the Compound A plus venetoclax combination again driving the tumors into regression as shown in FIG. 3.

Example 2: In Vivo Tumor Growth Inhibition in ABC-DLBCL Tumor Model

Female SCID Beige mice were implanted with SU-DHL-2 cells which harbor MYD88-S222R pathway activating mutations. The mice were treated with Compound A (100 mg/kg, qd, po, suspension in 0.5% Tween 20 and 0.25% hydroxyethyl cellulose), venetoclax (75 mg/kg, qd, po, solution in 60% phosal 50PG, 30% PEG 400, and 10% ethanol) or the combination for 27 continuous days.

All in life data acquisition, including body weight, tumor length, tumor diameter, tumor ulceration, clinical signs and animal mortality was collected in Study Director. Tumor ulceration was scored on a 6 level system with severity of 4 or higher requiring attention. At the end of the study (24 hours after the last dose), all surviving animals were examined externally for possible clinical abnormalities or adverse clinical signs, weighed and tumor measurements were taken for the last time.

Figure 4:
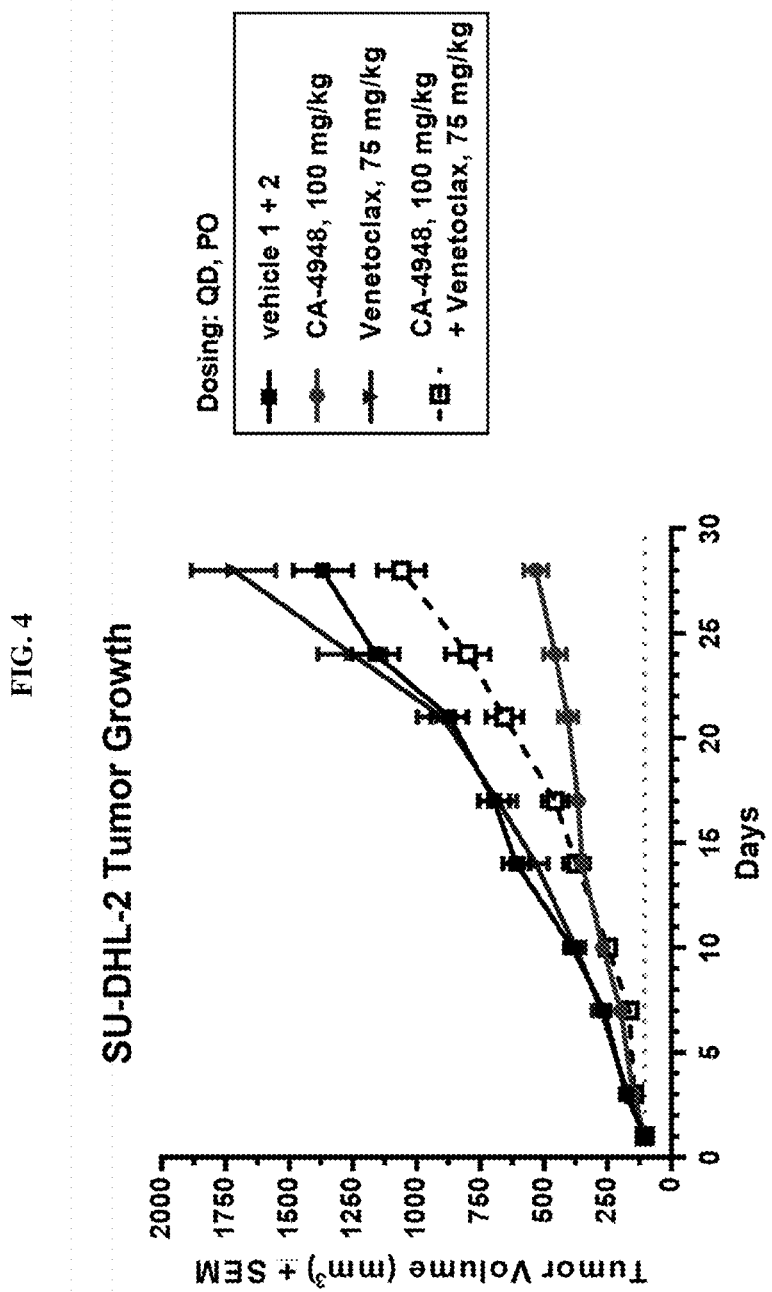
FIG. 4 shows the tumor growth response in three groups of tumor-bearing mice that had been treated with Compound A, venetoclax or a combination thereof, after 27 days of treatment.

Single agent treatment with Compound A exhibited moderate tumor growth inhibition (TGI) of 66% at day 28. No significant effect on tumor growth was observed with single agent treatment with Venetoclax. Treatment with a combination of Compound A and Venetoclax exhibited a TGI of 24% at day 28 (FIG. 4).

|  | Dosage (mg/kg) | TGI % (Day 28) | P value (t-test) | No. of mice (Day 28) |
| --- | --- | --- | --- | --- |
| Vehicle | — | na | na | 10/10 |
| CA-4948 | 100 | 66 | <0.0001 | 10/10 |
| Venetoclax | 75 | na | 0.1 | 10/10 |
| CA-4948 + Venetoclax | 100 + 75 | 24 | 0.053 | 10/10 |

Figure 5:
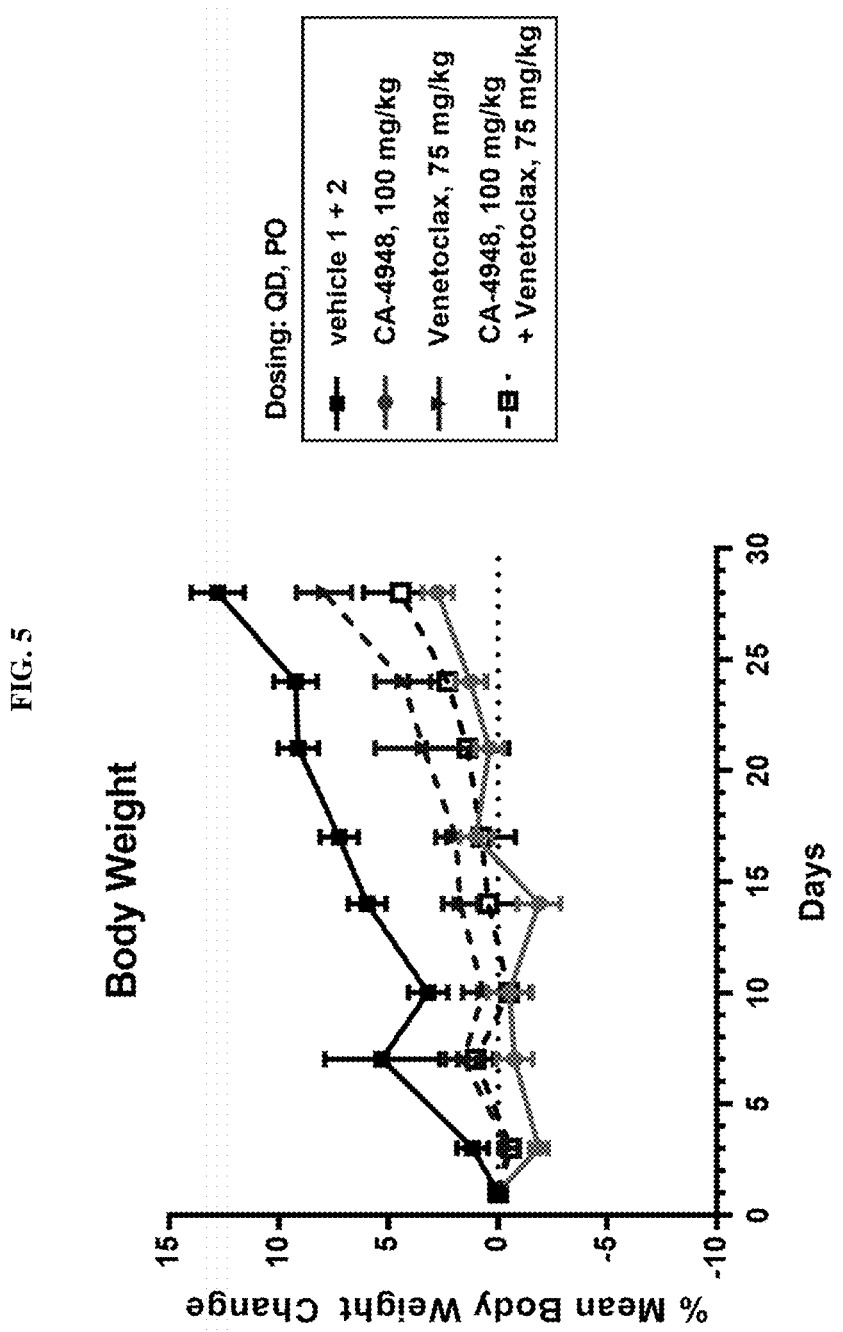
FIG. 5 shows the body weight change in three groups of tumor-bearing mice that had been treated with Compound A, venetoclax or a combination thereof.

The combination was tolerated at the end of treatment without body weight loss relative to predose weight (FIG. 5).

INCORPORATION BY REFERENCE

All publications and patents mentioned herein are hereby incorporated by reference in their entirety as if each individual publication or patent were specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

I claim:

1. A method of treating Diffuse Large B-cell Lymphoma (DLBCL) in a subject, comprising administering to the subject compound A and venetoclax, wherein compound A is:

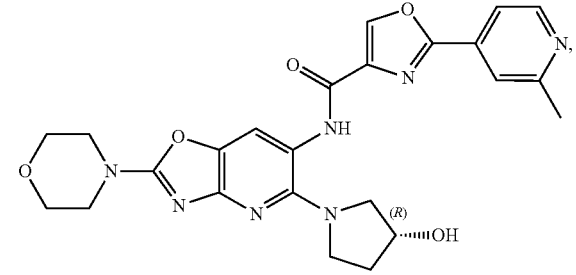

2. The method of claim 1, wherein the subject has a L265P mutation in MYD88.

3. The method of claim 1, wherein the DLBCL is activated B-cell subtype DLBCL.

4. The method of claim 1, wherein conjointly administering compound A and venetoclax provides improved efficacy relative to separately administering compound A or venetoclax.

5. The method of claim 4, wherein conjointly administering compound A and venetoclax provides a synergistic effect, as compared to the administration of compound A or venetoclax alone.

6. The method of claim 1, wherein the compound A and venetoclax are administered simultaneously.

7. The method claim 1, wherein the venetoclax is administered within about 5 minutes to within about 168 hours prior to or after administration of compound A.

* * * * *